United States Patent
Oda et al.

(10) Patent No.: US 10,460,187 B2
(45) Date of Patent: Oct. 29, 2019

(54) BIOMETRIC AUTHENTICATION DEVICE AND SYSTEM

(71) Applicant: Hitachi, Ltd., Tokyo (JP)

(72) Inventors: Masaru Oda, Tokyo (JP); Akira Omachi, Tokyo (JP); Yoshihiro Iwama, Tokyo (JP); Yusuke Daimon, Tokyo (JP); Daisuke Matsubara, Tokyo (JP); Hiroko Hasebe, Tokyo (JP); Akio Nagasaka, Tokyo (JP); Yusuke Matsuda, Tokyo (JP); Naoto Miura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/756,289

(22) PCT Filed: Dec. 18, 2015

(86) PCT No.: PCT/JP2015/085439
§ 371 (c)(1),
(2) Date: Feb. 28, 2018

(87) PCT Pub. No.: WO2017/104061
PCT Pub. Date: Jun. 22, 2017

(65) Prior Publication Data
US 2018/0247142 A1  Aug. 30, 2018

(51) Int. Cl.
*G06K 9/00* (2006.01)
*G07C 9/00* (2006.01)
(Continued)

(52) U.S. Cl.
CPC ........ *G06K 9/00885* (2013.01); *A61B 5/0077* (2013.01); *G01B 11/24* (2013.01);
(Continued)

(58) Field of Classification Search
CPC .................. G06F 16/583; G06F 21/32; G06K 2009/00932; G06K 9/00375;
(Continued)

(56) References Cited

U.S. PATENT DOCUMENTS 5,528,355 A * 6/1996 Maase ................ G06K 9/00046
356/71
6,349,227 B1 * 2/2002 Numada ................ A61B 5/061
600/309
(Continued)

FOREIGN PATENT DOCUMENTS

JP  2001-307102 A  11/2001
JP  2007-310429 A  11/2007
(Continued)

OTHER PUBLICATIONS

International Search Report of PCT/JP2015/085439 dated Feb. 16, 2016.

*Primary Examiner* — Dionne Pendleton
(74) *Attorney, Agent, or Firm* — Mattingly & Malur, PC

(57) ABSTRACT

A biometric authentication device including a housing, a light source unit that is installed on an upper surface of the housing and includes a light source, and an opening that is provided in the upper surface of the housing and located below the light source, and an imaging unit that is disposed inside the housing is disclosed. In the device, an optical axis of the light source intersects with a longitudinal direction of the housing, and the imaging unit images a user's biometric feature irradiated with an irradiation light from the light source through the opening.

8 Claims, 22 Drawing Sheets

(51) Int. Cl.
*G06F 16/583* (2019.01)
*G01B 11/24* (2006.01)
*G06F 21/32* (2013.01)
*A61B 5/00* (2006.01)
*G06T 7/00* (2017.01)
*H04L 29/06* (2006.01)
*G06K 9/20* (2006.01)

(52) U.S. Cl.
CPC ............ *G06F 16/583* (2019.01); *G06F 21/32* (2013.01); *G06K 9/00033* (2013.01); *G06K 9/00919* (2013.01); *G06K 9/2027* (2013.01); *G06T 7/0002* (2013.01); *G07C 9/00158* (2013.01); *H04L 63/0861* (2013.01); *G06K 9/00375* (2013.01); *G06K 2009/00932* (2013.01); *G06T 2207/10004* (2013.01)

(58) Field of Classification Search
CPC .......... G06K 9/00885; G06K 9/00919; G06K 9/2027; G06K 9/00013; G06K 9/00033; G06K 2009/0006; G06K 9/00; G06K 9/00912; G06K 9/20; G06K 9/00006; G06K 9/00026; G06K 9/00369; G06K 9/00382; G06K 9/00771; G06K 9/036; G06K 9/2018; G06K 9/6255; G06T 2207/30101; G06T 7/0012; G06T 7/30; G06T 2207/10004; G06T 7/0002; G06T 1/00; A61B 5/0059; A61B 5/061; A61B 5/1455; A61B 5/6826; A61B 5/6838; A61B 5/1171; A61B 2503/04; A61B 2560/0242; A61B 3/10; A61B 5/02007; A61B 5/0205; A61B 5/024; A61B 5/0816; A61B 5/1103; A61B 5/1113; A61B 5/117; A61B 5/1172; A61B 5/14532; A61B 5/4806; A61B 5/6821; H04N 5/33; H04N 5/2252; H04N 5/2354; H04N 5/335; H04N 7/183; H04N 7/188; E05B 81/76; G02B 5/0242; G02B 5/30; G07C 9/00158; G07C 9/00563; G16H 40/63; G16H 40/67; G16H 50/20; H04L 63/0861

See application file for complete search history.

(56) References Cited

U.S. PATENT DOCUMENTS

| | | | |
|---|---|---|---|
| 2001/0036297 A1 | 11/2001 | Ikegami et al. | |
| 2002/0028004 A1* | 3/2002 | Miura ................ | G06K 9/00006 382/124 |
| 2003/0133143 A1* | 7/2003 | McClurg ............ | G06K 9/00013 358/1.14 |
| 2004/0041998 A1* | 3/2004 | Haddad .............. | G06K 9/00033 356/71 |
| 2007/0106172 A1* | 5/2007 | Abreu .................. | A61B 5/0002 600/549 |
| 2007/0189597 A1* | 8/2007 | Limer ....................... | A61J 7/02 382/153 |
| 2008/0063243 A1 | 3/2008 | Kiyomizu et al. | |
| 2008/0107309 A1* | 5/2008 | Cerni ................ | G06K 9/00033 382/115 |
| 2013/0120760 A1* | 5/2013 | Raguin .................. | G01B 11/24 356/612 |
| 2013/0329031 A1* | 12/2013 | Miura ................ | G06K 9/00013 348/77 |
| 2017/0143241 A1* | 5/2017 | McBain .............. | B64D 45/0015 |
| 2018/0052958 A1* | 2/2018 | Crawford ................ | G06F 21/62 |
| 2018/0121643 A1* | 5/2018 | Talwerdi ................ | G06F 21/32 |
| 2018/0268193 A1* | 9/2018 | Badzinski .......... | G06K 9/00033 |

FOREIGN PATENT DOCUMENTS

| | | |
|---|---|---|
| JP | 2008-065570 A | 3/2008 |
| WO | 2013/076858 A1 | 5/2013 |
| WO | 2015/141007 A1 | 9/2015 |

* cited by examiner (A)  (B)

BIOMETRIC AUTHENTICATION DEVICE AND SYSTEM

TECHNICAL FIELD

The present invention relates to a device and a system for authenticating an individual with the use of human biological information.

BACKGROUND ART

In order to perform a person's identification, techniques leveraging human biological information have been put into practical use. For example, as a personal authentication of a bank terminal, a vein authentication technology for performing authentication with the use of a pattern of veins of hand's fingers or a palm has been known.

PTL 1 discloses an example in which such a vein authentication technology is applied to a gate of a railway station or an event holding venue and used for management of a visitor.

CITATION LIST

Patent Literature

PTL 1: Japanese Patent Application Laid-Open Publication No. 2007-310429

SUMMARY OF INVENTION

Technical Problem

PTL 1 discloses the example in which the vein authentication technology is applied to the gate. However, PTL 1 discloses a type in which authentication is performed by inserting the hand into a slit-like interface. In order to enhance user's convenience, for example, it is desirable to use a type capable of performing the authentication by simply holding a card (in the case of biometric authentication, a hand or the like) over an upper surface of a device casing as currently used in automatic ticket gates at railroads. However, in an environment frequently used by a large number of unspecified people, there is a problem to be considered in order to put a gate employing the vein authentication technology into practical use.

In other words, it is desirable to complete the authentication in a short time when a user enters at a short time interval, for example, like the gates of the railway station or the event holding place. In order to achieve the above desire, there is a need to acquire clear biological information (for example, a vein image) for the purpose of avoiding authentication errors as much as possible. In order to achieve the acquisition, it is desirable to keep a relative positional relationship between a body pare (for example, a hand or fingers) used for authentication and a light source as well as an imaging unit for acquiring an image as constant as possible.

However, the large number of unspecified users are different from each other in a proficiency level of how to use the authentication device. Since the user low in the low proficiency level has less knowledge about a correct presentation position and a correct presentation posture of a biological body, the user may present the biological body with an incorrect position and an incorrect posture and authentication accuracy may be deteriorated. In addition, it is not realistic to force the users to perform complex actions in order to pass through the gate in a short time.

An object of the present invention is to provide a biometric authentication gate device and system which are capable of performing accurate biometric authentication while reducing a burden on a user.

Solution to Problem

In order to address the problem described above, according to one aspect of the present invention, there is provided a biometric authentication device including: a housing; a light source unit that is installed on an upper surface of the housing and includes a light source; an opening that is provided in the upper surface of the housing and located below the light source; and an imaging unit that is disposed inside the housing. The device is configured such that an optical axis of the light source intersects with a longitudinal direction of the housing and images a biometric feature of a user irradiated with an irradiation light from the light source through the opening by the imaging unit.

In an example of a more specific configuration, the light source is a light source array in which a plurality of point light sources are two-dimensionally arranged, a surface formed by the light source array intersects with the longitudinal direction of the housing at an angle of less than 90 degrees, and optical axes of a majority of the plurality of point light sources intersect with the longitudinal direction of the housing at an angle of less than 90 degrees.

In another example of the specific configuration, the opening is disposed on a front side of the housing in the longitudinal direction, the light source unit is disposed on a far side of the housing in the longitudinal direction, and the opening and the light source unit are disposed so as not to overlap with each other in the longitudinal direction of the housing.

In another example of the more specific configuration, a direction that connects the opening and the light source is inclined at a predetermined angle with respect to the longitudinal direction.

In another example of the more specific configuration, a marker is placed on the upper surface of the housing between the opening and the light source unit.

According to another aspect of the present invention, there is provided a biometric authentication device including: a housing; a light source unit that is installed on an upper surface of the housing and includes a light source; an opening that is provided in the upper surface of the housing; and an imaging unit that is disposed inside the housing. In the device, a line that connects a projection point S of a geometric center of gravity of the light source on a floor surface and a projection point O of the geometric center of gravity of the opening on the floor surface intersects with the longitudinal direction of the casing at an angle other than 90 degrees. The floor surface a virtual surface on which the housing is installed and is usually a surface perpendicular to a direction of gravity.

In an example of the more specific configuration of the present invention, the light source is a light source array in which a plurality of point light sources are two-dimensionally arranged, and the geometric center of gravity of the light source is the geometric center of gravity of a surface formed by the light source array.

In an example of the more specific configuration according to the present invention, the optical axes of irradiation lights from the majority of the plurality of point light sources intersect with the longitudinal direction of the housing at an angle of less than 90 degrees.

According to another aspect of the present invention, there is provided a biometric authentication system including: a biometric authentication device, a registration device, and a storage device. In the system, the biometric authentication device includes: a housing; a light source unit that is installed on an upper surface of the housing and includes a light source; an opening that is provided in the upper surface of the housing and located below the light source; and an imaging unit that is disposed below the opening. Further, the biometric authentication device is configured such that an optical axis of the light source intersects with a longitudinal direction of the housing at an angle of less than 90 degrees, and images a biometric feature of a user irradiated with an irradiation light from the light source through the opening by the imaging unit. In addition, the registration device according to the system acquires the biometric feature of the user and registers the acquired biometric feature as reference data in the storage device. Moreover, the storage device of the system stores the reference data. The biometric authentication system has a function of performing the user's authentication with the use of the biometric feature of the user imaged by the biometric authentication device and the reference data as a whole.

Advantageous Effects of Invention

According to aspects of the present invention, there can be provided the biometric authentication device and system which are capable of performing an accurate biometric authentication while reducing a burden on a user.

DESCRIPTION OF EMBODIMENTS

Figure 1:
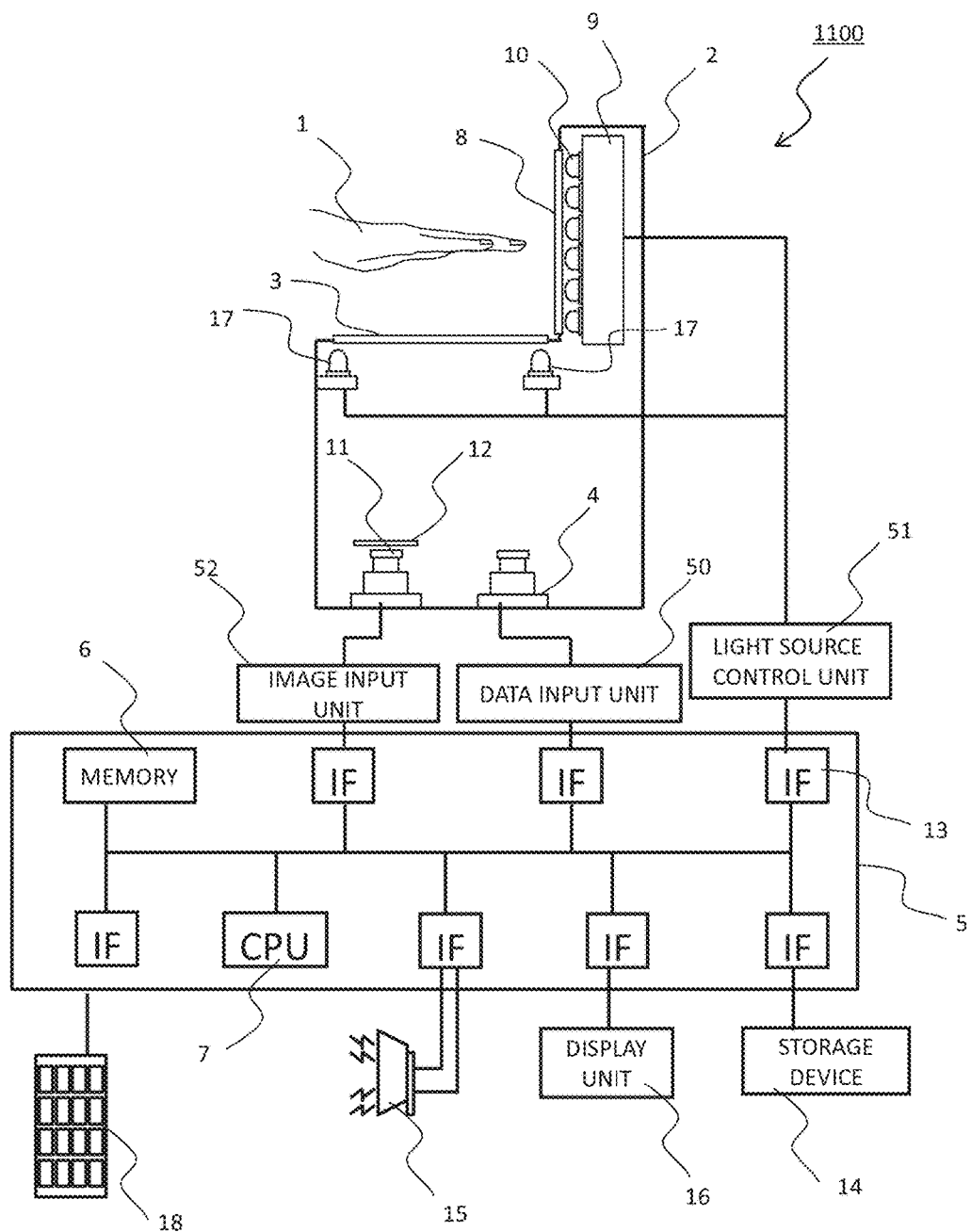
FIG. 1 is a block diagram of a biometric authentication system according to an example of the present invention.

An embodiment will be described in detail with reference to the accompanying drawings. However, the present invention should not be construed as being limited to the description of the embodiment described below. It will be easily understood by those skilled in the art that a specific configuration can be changed without departing from the spirit or scope of the present invention.

In the configuration of the invention described below, the same reference numerals are used for the same parts or parts having similar functions in different drawings, and a redundant description may be omitted.

The notations such as "first", "second", and "third" in the present specification and the like are attached to identify components, and do not necessarily limit the number or order. The number for identifying the component is used for each context and the number used in one context does not necessarily indicate the same configuration in other contexts. The component identified by a certain number does not preclude the function of the component identified by other numbers.

In order to facilitate the understanding of the invention, the position, size, shape, range, and so on of each configuration shown in drawings or the like may not indicate the actual position, size, shape, range, and so on. Therefore, the present invention is not necessarily limited to the position, size, shape, range and so on disc nosed in drawings and the like.

Components expressed in the singular in the present specification include the plural unless the singular is explicitly indicated in a particular context.

<1. Basic Configuration of Authentication Device>

In describing an example, first, an example of a basic configuration in which a sharp finger vein image is captured to perform authentication will be described. In the present specification, for the sake of convenience, an entire configuration for performing a biometric authentication process is referred to as a "biometric authentication system", and a configuration that accesses a biological body for performing the biometric authentication process (for example, a configuration including an imaging unit) is referred to as a "biometric authentication device." The biometric authentication device usually includes a single or multiple housings which are installed at one position and internal configurations of the housings. The biometric authentication device alone may configure the biometric authentication system. In addition, the biometric authentication device may configure only a part of the biometric authentication system in some cases.

For example, when the biometric authentication device is used for a gate for an entry and exit management, the biometric authentication device can executes processing up to a personal authentication within a housing installed at the gate. Alternatively, the authentication process per se may be executed by an authentication unit of a server or the like which is connected to the housing installed at the gate through a network and installed at a remote place, and the housing installed at the gate may configure the biometric authentication device having only a blood vessel image acquisition function for transmitting information on the imaged blood vessel to the authentication unit. As described above, in the present description, a device alone which has only the blood vessel image acquisition function but does not have the authentication function is also referred to as the biometric authentication device.

FIG. 1 is a schematic block diagram of a biometric authentication system according to the present example.

Figure 2:
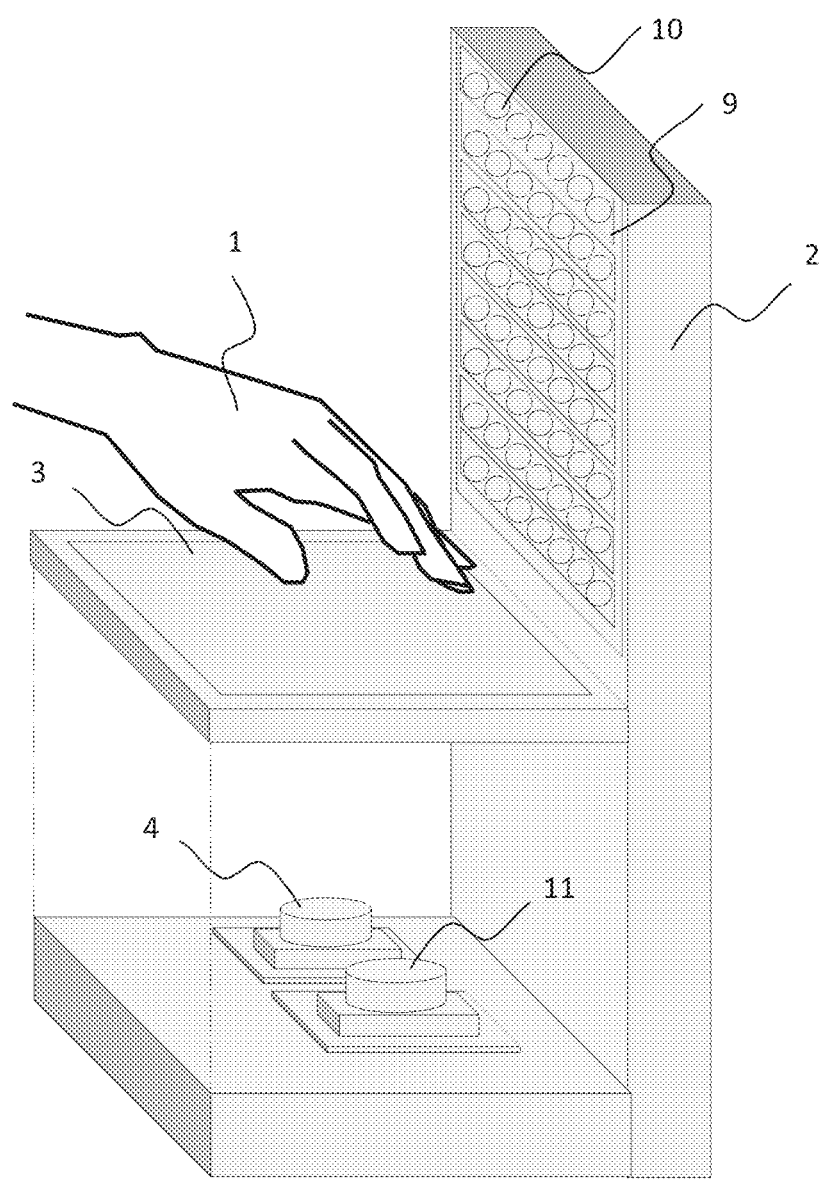
FIG. 2 is a perspective view showing a part of a biometric authentication device according to the example of the present invention.

FIG. 2 is a perspective view showing an image acquisition device (image acquisition unit) that captures a finger vein image in the biometric authentication device according to the present example.

In a biometric authentication system 1100 according to the present example, an opening 3 is provided in a surface of a housing of an image acquisition device 2 so as to present a hand 1 above the opening (or a hand presentation unit) 3 of the image acquisition device (image acquisition unit) 2 at the time of capturing a blood vessel image of fingers. A distance sensor 4 disposed inside the housing below the opening 3 converts a light received for a distance measurement into an electric signal and takes in the converted electric signal into a computer 5 through a data input unit 50 as data reflecting a distance between the hand 1 and the distance sensor 4. A CPU 7 calculates a position of the hand 1, a posture of the hand 1, positions of the fingers, postures of the fingers, and so on based on data captured by the computer 5 according to a program stored in a memory 6.

A light source control unit 51 controls a light source array 9 that is disposed inside the opening (or an infrared ray irradiation unit) 8 based on the calculated positions and postures of the hand 1 and the fingers, select one or more irradiation light sources from multiple point light sources 10 configuring the light source array 9, and applies the irradiation light to the fingers. The light source array 9 is configured in such a manner that the point light sources 10 that are configured by, for example, light emitting diodes (LED) emitting infrared rays are arrayed two-dimensionally.

An imaging unit (for example, an infrared camera) 11 that is disposed below the opening 3 receives the light that has passed through an optical filter 12. The optical filter 12 is used to remove wavelengths unnecessary for acquiring, for example, a finger vein pattern. Meanwhile, one point light source 10 may be selected as the irradiation light source, but in the present example, in view of a fact that a hand movement area and an imaging area are large, it is desirable to select multiple consecutive point light sources 10 as one set. The light sources can be configured by known infrared diodes or the like.

The light is converted into an electric signal by the imaging unit 11 and captured as an image by the computer 5 through an image input unit 52. The captured image is once stored in the memory 6. Then, the CPU 7 checks one or more images stored in the memory 6 against one or more images stored in advance in a storage device 14 according to the program stored in the memory 6, and performs authentication.

An irradiation light from the point light sources 10 is irradiated onto the multiple fingers, thereby being capable of imaging blood vessels of the multiple fingers at the same time. In the calculation of the position and posture of the hand 1, the position and the posture of the hand may be detected with the use of an image of the hand captured by the imaging unit 11, or both of the image of the hand 1 captured by the imaging unit 11 and distance data between the hand 1 and the distance sensor 4 may be used.

The user can be informed of the authentication result by voice with the use of a speaker 15 and likewise the authentication result can be displayed on a display unit 16 so as to be informed the user. Visible light sources 17 are provided around the opening 3 and can inform the user of an authentication processing state in such a manner that the presented hand 1 is detected at the time of standby, and the visible light sources emit light with respective different colors at the time of an authentication process, an authentication success, and an authentication failure. In addition, a password and an ID can be input to a keyboard 18 to identify a registrant, and then a hand can be presented to perform authentication (1:1 authentication).

A transparent member (an infrared irradiation unit cover) made of acrylic, glass, or the like can be provided in the opening 3 or an opening 8. A film that cuts a visible light and allows only a near infrared light to pass through the film can be loaded in the opening 3 or the opening 8 so that the user cannot see the inside of the device.

The light source array 9 is disposed on a side of the opening 3. The light source array 9 is disposed on the side of the opening 3, in particular, on a front side of the user who presents the hand 1, thereby being capable of providing an open space in a moving direction and an upward direction when the user performs the authentication while moving, and being capable of improving the convenience of the user.

Multiple point light sources 10 are arrayed in a lattice pattern in the light source array 9. In the example of FIGS. 1 and 2, a surface configured by the light source array 9 is disposed in a direction perpendicular to an opening surface of the opening 3. However, those surfaces are not necessarily in a vertical relationship, and the surface of the light source array 9 may be disposed at an acute angle to the opening surface.

<2. Control of Light Source>

Figure 3:
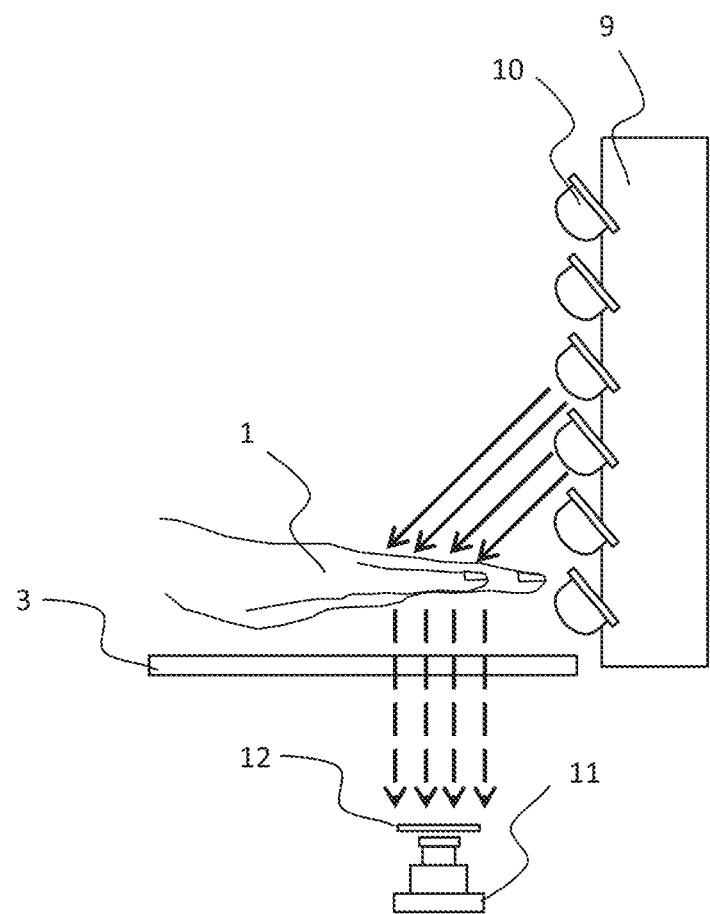
FIG. 3 is a side view showing a principle of imaging finger veins by applying an irradiation light from a light source to a finger.

A method of controlling the light source array 9 for capturing a clear finger vein image will be described with reference to FIG. 3. In the method of imaging the blood vessels of the fingers, for example, the fingers on a back of the hand is irradiated with the irradiation light (a near infrared light) from the light source array 9, and the imaging unit 11 receives the light that has passed through the fingers, thereby being capable of capturing the blood vessel image.

The reason why the control of the light source array 9 is preferable in imaging the finger veins in the image acquisition device 2 will be described as follows: When all of the point light sources 10 configuring the light source array 9 are turned on at the time of capturing the blood vessel image, a lot of light enters the opening 3 in a state where the hand is not presented. Furthermore, when the hand 1 is presented while all of the point light sources 10 are turned on, there is a possibility that an area of the hand is saturated with luminance and highlights are blown out. When an exposure time is shortened or the amount of light of the respective point light sources 10 is reduced for the purpose of preventing the blown out highlights, the amount of light passing through the fingers decreases, and furthermore, the blood vessel image to be captured becomes unclear due to the presence of the irradiation light from the point light sources 10 which has not passed through the fingers in the opening 3.

In addition, in the configuration of the device, because the entire hand 1 including not only the fingers but also the palm and the like can be presented in the opening 3, it is desirable that the opening 3 is shaped to be wider than the device assumed to present only the fingers. However, since a probability that a light unnecessary for imaging enters the opening 3 increases, a risk of hindering imaging of transmitted light having a small amount of light transmitted through the fingers increases.

Therefore, in order to capture a clear blood vessel image, it is desirable to ideally irradiate only the fingers with the irradiation light from the light source array 9 and increase the amount of light passing through the fingers. However, even if only the fingers are tried to be irradiated with the light while controlling the light source array 9, when the multiple fingers are irradiated with the light at the same time for the purpose of imaging the multiple fingers, it is difficult to prevent the irradiation light from passing through between the fingers.

Figure 4:
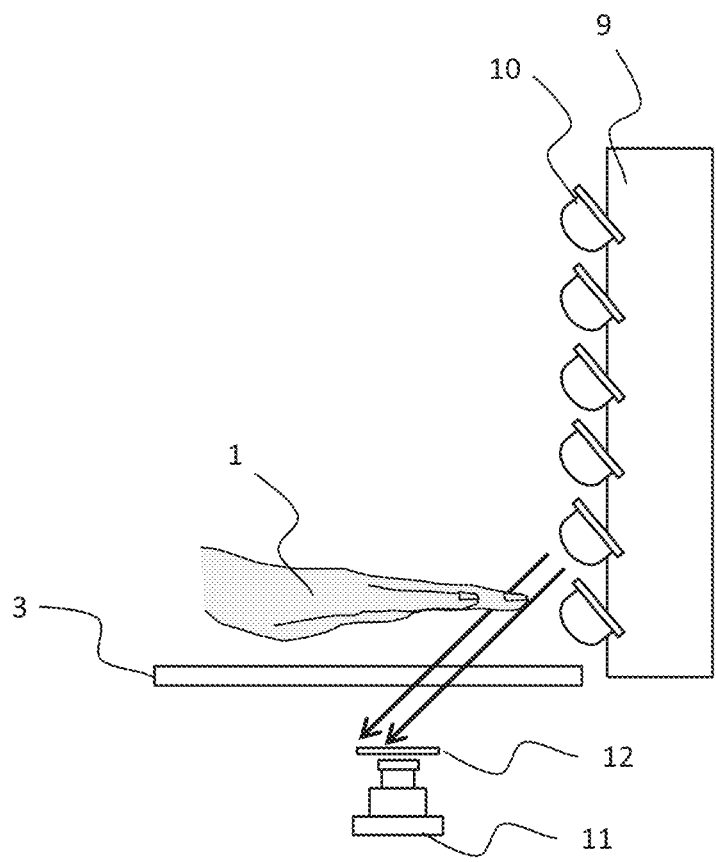
FIG. 4 is a side view showing a state in which an irradiation light passes through between fingers.

FIG. 4 shows how the hand 1 is irradiated with the light from the light source array 9 disposed at a position close to the opening 3. In this way, the light sources 10 disposed at the position close to the opening 3 have a high probability that the light passes through between the fingers, and when the irradiation light of the point light sources are directly received by the imaging unit 11, the brown out highlights (saturation of luminance) occur, making it difficult to image the clear blood vessel.

Figure 5:
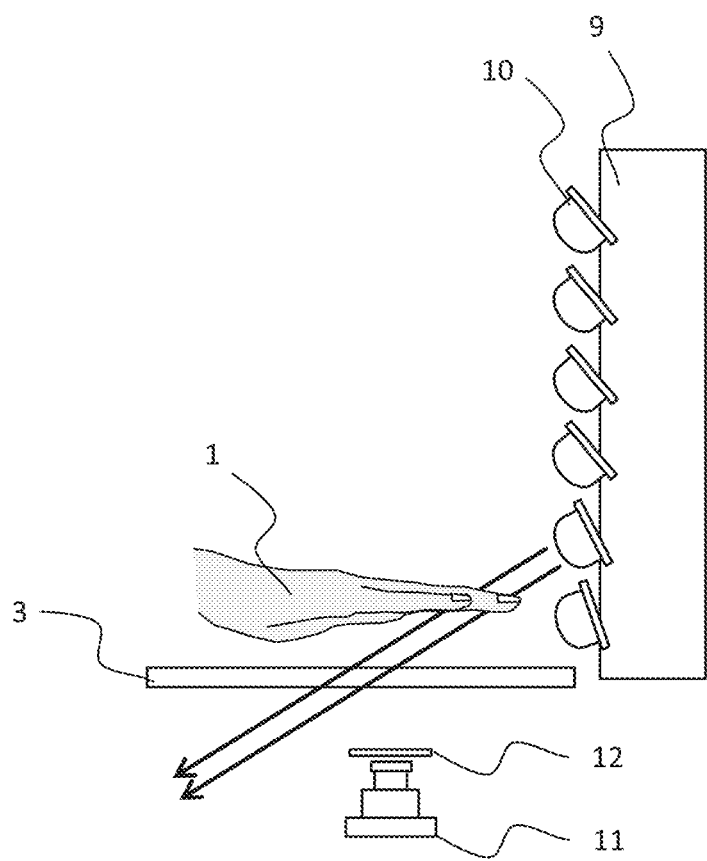
FIG. 5 is a side view showing an example of a point light source arrangement in which an irradiation light that has passed between the fingers is unlikely to be directly received by an imaging unit.

FIG. 5 shows an example in which the placement of the light sources is improved. As shown in FIG. 5, even when the irradiation light enters the opening 3 without being irradiated onto the fingers as shown in FIG. 5, it is desirable to place the light sources in such a manner that an angle of an acute angle formed by the optical axis of each light source 10 and the opening surface of the opening 3 is smaller as the light source 10 is closer to the opening, in other words, the light source is disposed at a lower side of an installation surface so that the probability that the irradiation light is directly received by the imaging unit 11 is low. With the above configuration, a possibility that the luminance is saturated is reduced, and the clearer blood vessel can be imaged.

<3. Authentication Processing Flow>

Figure 6:
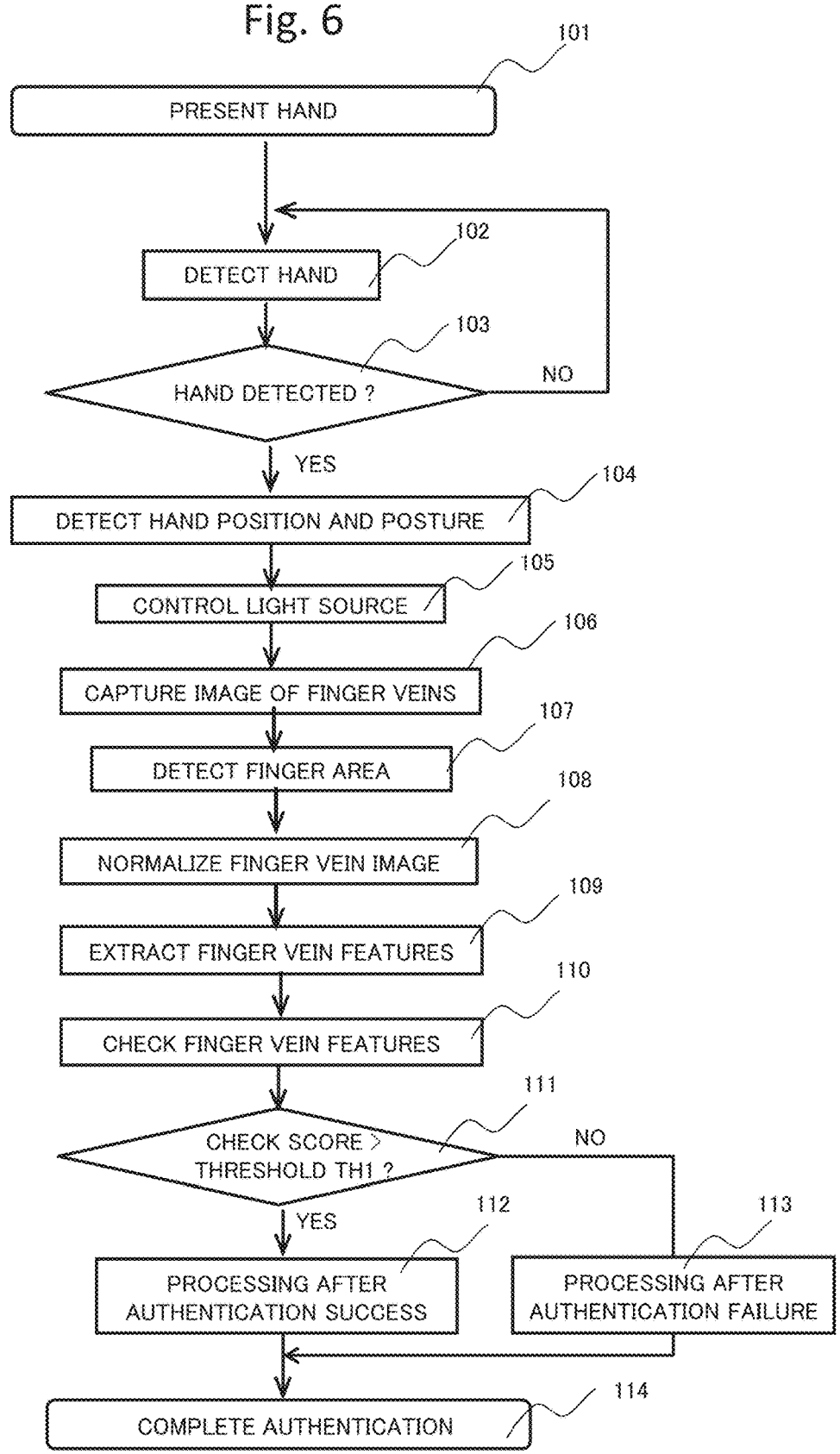
FIG. 6 is a flowchart of an authentication process leveraging a finger vein image captured while controlling the light source.

FIG. 6 shows a flowchart of the authentication process using the finger vein image captured while controlling the light amount of the irradiation light from the light source array 9. First, the user presents his hand to an upper portion of the opening 3 in Step 101, and the hand is detected in Step 102. The hand is detected based on the distance data acquired by the distance sensor 4 and it is determined whether the hand has been detected, or not, in Step 103. If no hand is detected, the flow returns to the detection of the hand in Step 102.

If the hand has been detected, a process of detecting the position and posture of the hand in Step 104 is performed in other words, position information and posture information based on a three-dimensional shape of the hand are detected and acquired. The light source array 9 is controlled in Step 105 according to the position of the hand and the posture of the hand detected in Step 104, to select and turn on only one or more point light sources 10 selected for imaging the blood vessel of the fingers.

After the point light sources 10 have been turned on, the imaging unit 11 images the finger veins in Step 106. Next, multiple finger areas in the finger vein image are detected in Step 107, and a normalization process such as a rotation correction of the fingers in each of the finger areas or a correction of distortion caused by a posture variation of the fingers is performed in Step 108. After the normalization of the finger vein image, blood vessel features are extracted from each finger vein image in Step 109.

The extracted blood vessel features are checked against data (reference data) indicating the blood vessel features that have already been registered in the storage device 14 to calculate a check score in Step 110. If the check score is larger than a predetermined threshold TH1 in Step 111, a process for opening the gate to enable a user's entry or the like after authentication success in Step 112. If the check score is equal to or lower than the TH1, a process after authentication failure is performed in Step 113 and the authentication flow is completed in Step 114.

<4. Example of Authentication System and Registration Device over Network>

Figure 7:
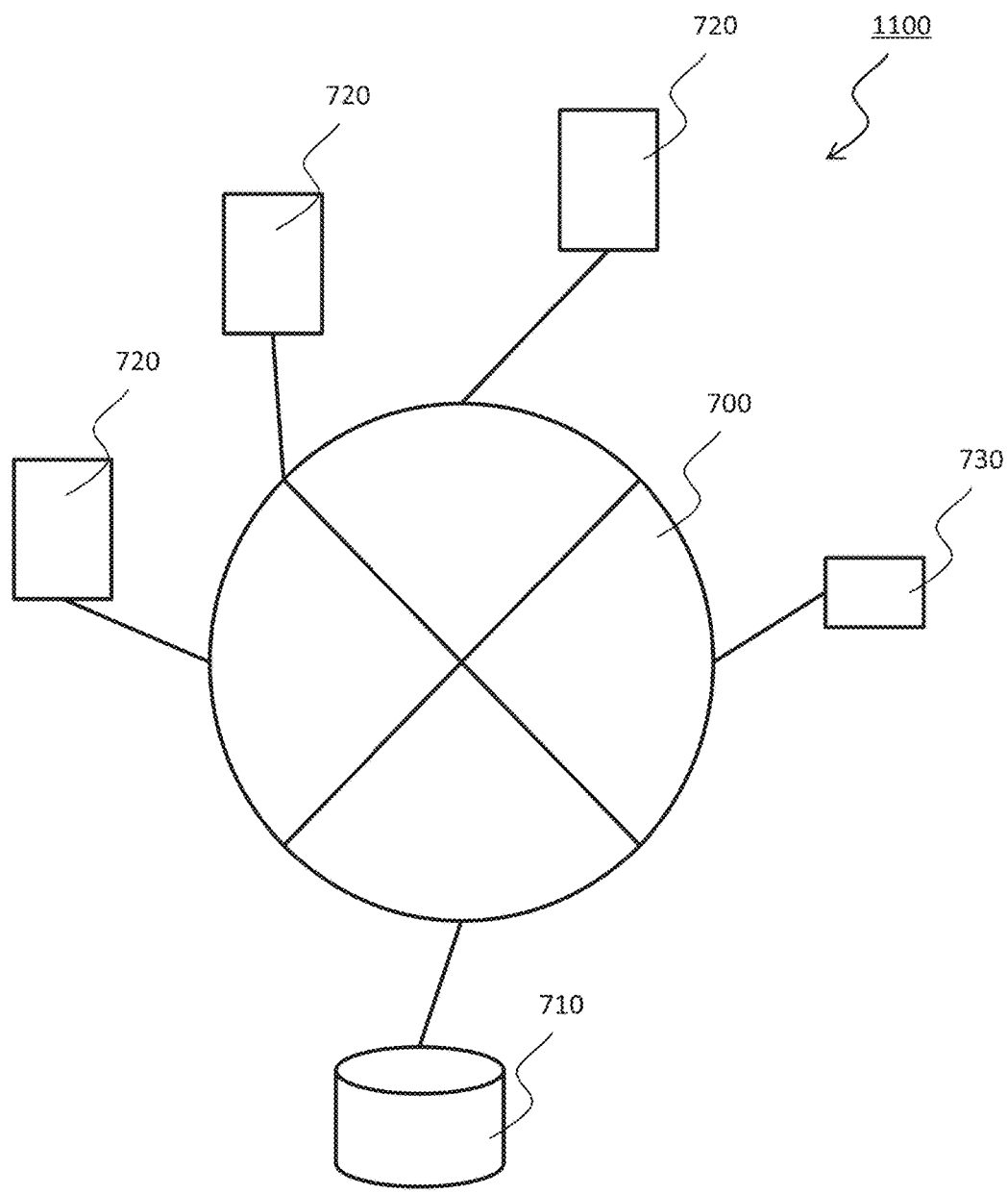
FIG. 7 is a configuration diagram of a biometric authentication system according to the example of the present invention.

FIG. 7 is a diagram showing an example of a system in which the biometric authentication system 1100 shown in FIGS. 1 and 2 is configured by a network. The biometric authentication system 1100 is functionally equivalent to the configuration described in FIGS. 1 and 2. In the example of FIG. 1, however, the data (reference data) indicating the blood vessel features to be checked is stored in the storage device 14. On the other hand, in the example of FIG. 7, the reference data is stored in a data server 710 connected over a network 700.

Multiple biometric authentication devices 720 can be connected to the network 700, and each of the biometric authentication devices 720 shown in FIG. 7 acquires the reference data from the data server 710 at the time of authentication and performs an authentication process. Alternatively, each of the biometric authentication devices 720 may transmit an acquired image of the blood vessel to the data server 710 at the time of authentication, and the data server 710 may perform the authentication process and return only a result to the biometric authentication device 720. For that reason, the biometric authentication device 720 may be configured such that, for example, the storage device 14 for storing the reference data is omitted from the configuration of FIGS. 1 and 2, and an interface for connecting to the network 700 is added.

A registration device 730 is a device for acquiring image data indicating the blood vessel features for registration of the reference data. The image data acquired by the registration device 730 is transmitted to and stored in the data server 710. The configuration of the registration device 730 is basically the same as that of the biometric authentication device 720 in FIG. 7, but a configuration for acquiring the image data indicating the blood vessel features, that is, the image acquisition device 2 shown in FIGS. 1 and 2 and an required I/O interface may be provided, and no configuration for authentication (checking) is required.

Since the image acquisition device 2 in FIG. 2 can acquire the blood vessel features of the multiple fingers at the same time, if the image acquisition device 2 is used for the registration device 730, an ID of the registrant can be registered in association with the blood vessel features of the multiple fingers. In order to perform authentication with high accuracy, it is desirable that the blood vessel features of the multiple fingers can be registered with the use of the blood vessel images at the moment when the blood vessels of all the fingers are sharply imaged. If the blood vessels of all the fingers cannot be clearly imaged at the same time, a registration processing period is set, and the blood vessel features in the image at the moment when the blood vessel is clearly imaged for each finger among the images captured within the period can be registered. In the registration processing period, guidance information of the posture of the hand to be presented by the registrant can be displayed on the display unit 16 and a voice guidance can be performed by the speaker 15.

When a variation in the postures of the hand and the fingers is large, since an illumination condition by the irradiation light from the light source array 9 also changes, even if only the blood vessel features imaged in a presentation posture of one hand are registered, authentication may not deal with any posture variation. Therefore, the blood vessel features imaged with multiple postures of the hand and the fingers can be registered, thereby being capable of performing authentication with various hand presentation postures.

In order to prevent the registration of counterfeited artifacts, a gesture recognition of the presented hand is performed at the time of registration, and the registrant is made to perform a designated gesture to reject a forged object (artifact) such as a rigid body.

<5. Examination of Positional Relationship Between Hand and Light Sources at the Time of Imaging Blood Vessels>

Figure 8:
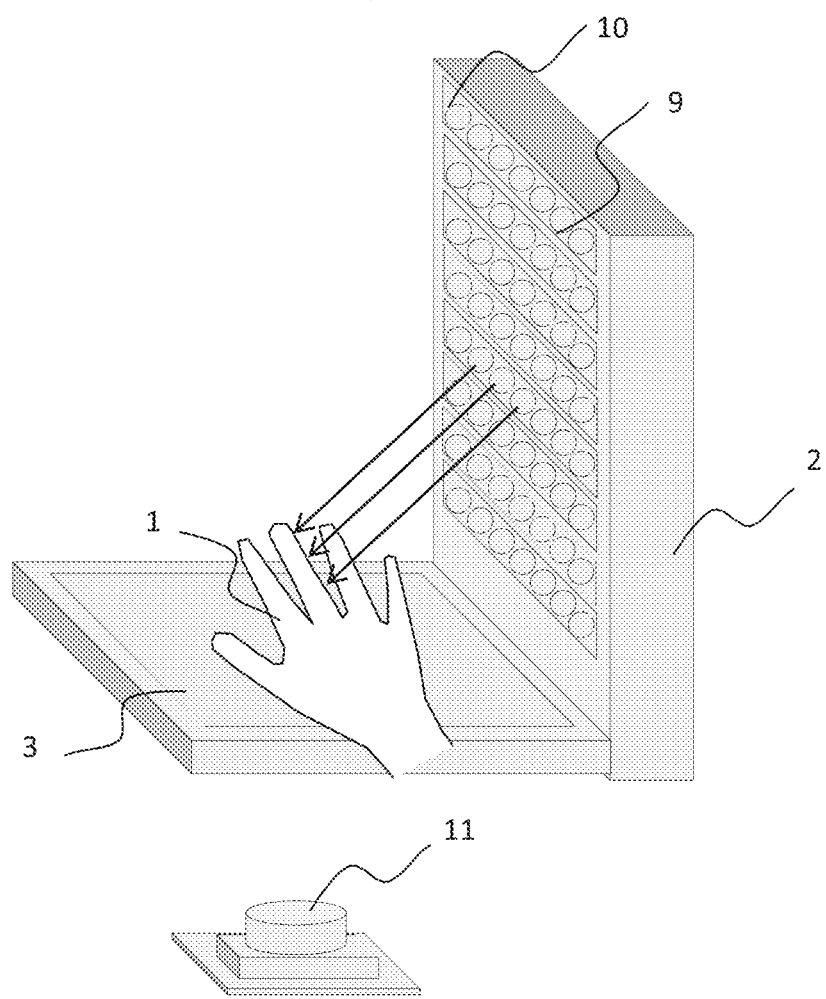
FIG. 8 is a perspective view showing a situation in which irradiation light is irradiated from a side surface of a finger of a hand to capture a finger vein image.

FIG. 8 shows a state of imaging the blood vessel image of the fingers by irradiating a light from a side surface of the hand.

Figure 9:
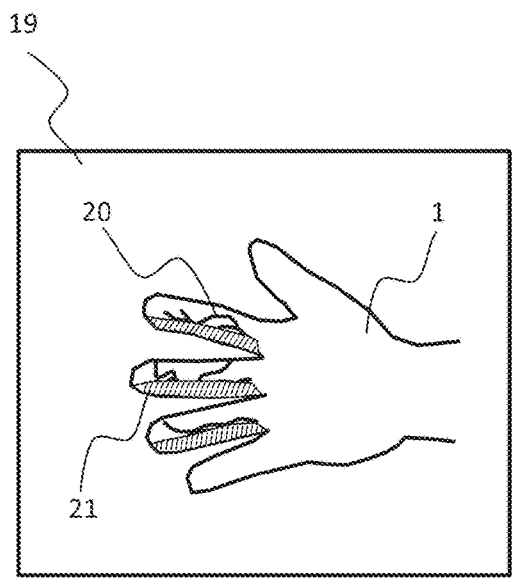
FIG. 9 is a plan view showing an example of the finger vein image including a luminance saturation region photographed in FIG. 8.

FIG. 9 is a schematic diagram of the blood vessel image of the fingers imaged in the state of FIG. 8.

As shown in FIG. 8, when the hand is presented on an imaging surface of the imaging unit 11, the side surfaces of the fingers are irradiated with the irradiation light from the point light sources 10, and a reflected light is received by the imaging unit 11. For that reason, in a blood vessel image 19 captured by the imaging unit 11, as shown in FIG. 9, luminance saturation areas 21 are generated on one side half surfaces of the fingers of the hand 1. In addition, the light is blocked by the side surfaces of the fingers so that a shadow is generated on parts of the adjacent fingers, resulting in a possibility that the blood vessel images cannot be acquired.

In order to avoid the problem described above, it is preferable to irradiate the irradiation light so that the side surfaces of the fingers are not irradiated with the irradiation light from the point light sources 10 as much as possible. In other words, the irradiation light is irradiated from a longitudinal direction of the fingers, thereby being capable of avoiding the problem that the side surfaces of the fingers are irradiated with the irradiation light.

Figure 10:
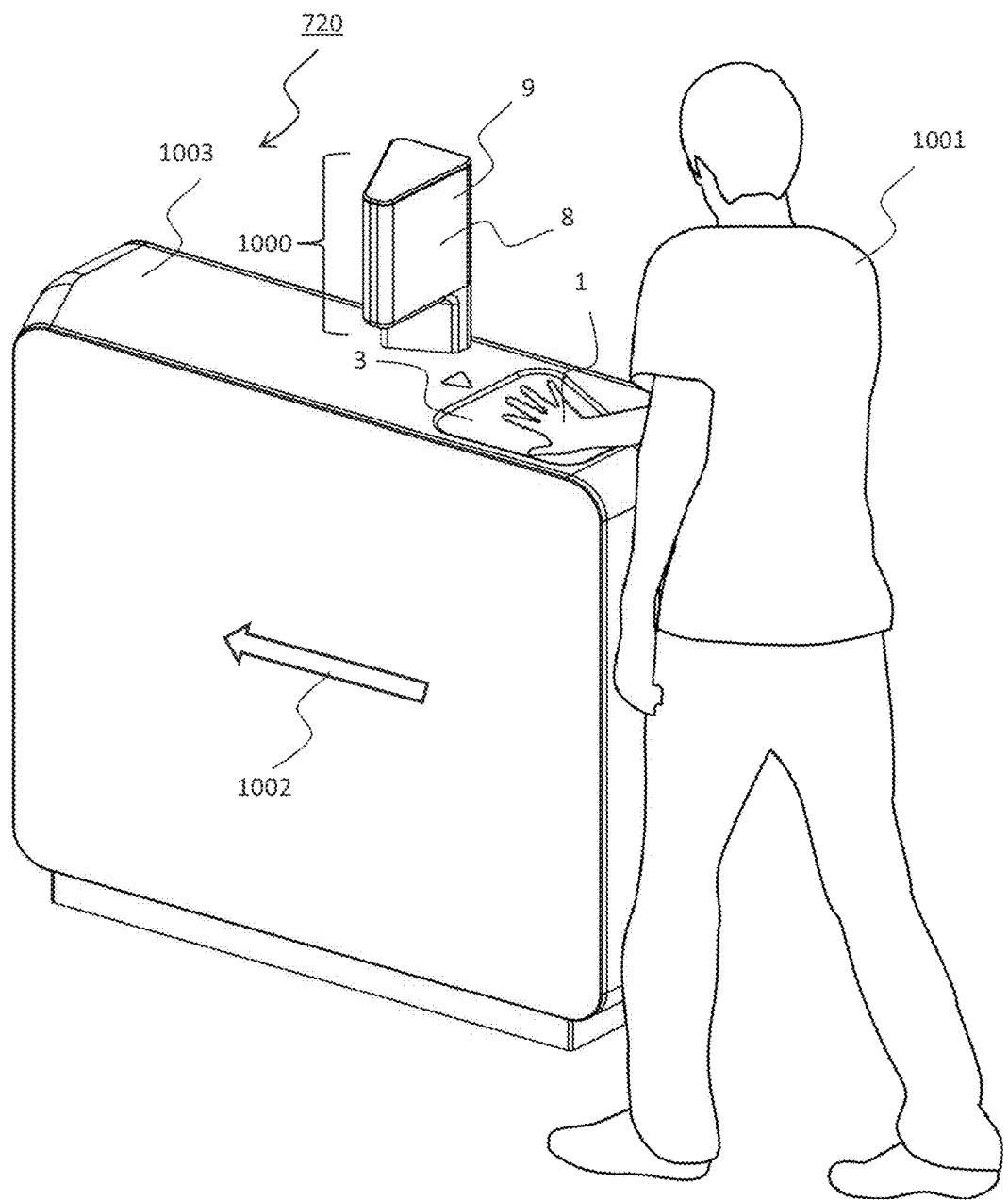
FIG. 10 is a perspective view showing a situation in which the user uses the biometric authentication device according to the example of the present invention.

FIG. 10 shows an example of a case in which the biometric authentication device 720 is configured as a walk-through type finger vein authentication device for use as the gate, and in the walk-through type finger vein authentication device, it is desirable that the authentication unit is placed at a position where the hand can be easily held toward a user's traveling direction, and the authentication can be performed without stopping walking.

In the example of FIG. 10, it is assumed that the biometric authentication system is connected by the network shown in FIG. 7 in FIG. 10, although not shown because of an internal configuration, as with the configuration of FIG. 2, the light source array 9 is configured in such a manner that the multiple point light sources 10 are two-dimensionally arranged inside the opening 8. A configuration in which the light source array 9 is stored and is placed on an upper surface of a housing 1003 of the biometric authentication device 720 is referred to as a light source unit 1000 (or a light irradiation unit) for convenience. The upper surface is a surface of the housing 1003 on a side of the housing 1003 opposite to the ground surface.

In addition, similarly, although not shown because of the internal configuration, as with the configuration of FIG. 2, the imaging unit 11, the optical filter 12, and the distance sensor 4 are disposed below the opening 3, and receive a light entering through the opening 3. In addition, the memory 6, the CPU 7, the interface 13, the image input unit 52, the data input unit 50, the light source control unit 51, and so on as required are arranged inside the housing 1003. The interface 13 has a function of communicating with the data server 710 over the network 700. Further, the storage device 14, the speaker 15, the display unit 16, and the keyboard 18 may be added as necessary.

The hand 1 is irradiated with the irradiation light from the internal point light sources 10 through the opening 8 of the light source unit 1000. The irradiation light irradiated to the hand 1 passes through the opening 3 and is imaged by the imaging unit 11 located inside the housing 1003 of the biometric authentication device 720. A pattern of veins of the fingers is acquired from the image acquired by the imaging unit 11. The acquired pattern is checked against the reference data stored in the data server 710 over the network 700 to perform the authentication. The configuration of the biometric authentication device 720 is different in contour from that of the biometric authentication device in FIGS. 1 and 2, but the functions of the respective components are identical with those described in FIGS. 1 and 2.

Now, a user 1001 is going to perform authentication with the authentication biometric authentication device 720 while moving in a direction of an arrow indicating a traveling direction 1002. When the user 1001 is going to perform authentication with the biometric information of the hand 1 in such a situation, the user usually sticks out the hand 1 forward in order to perform the authentication more quickly. Therefore, in order to irradiate the irradiation light from the longitudinal direction of the fingers of the hand, the light source unit 1000 is to be placed at a position where the hand 1 is disposed, that is, is to be placed in front of the opening 3.

However, the housing 1003 and the light source unit 1000 of the biometric authentication device 720 are to be positioned beside a movement path of the user 1001 so as not to obstruct the movement of the user 1001. Therefore, the biometric authentication device 1003 and the light source unit 1000 of the biometric authentication device 720 are positioned in front of and at a side of (that is, diagonally in front of) the user 1001 at the time of authentication operation and a configuration in which the irradiation light is irradiated from the longitudinal direction of the fingers of the hand of the user 1001 is required. FIG. 10 shows an example of the biometric authentication device 720 which satisfies the above conditions. The irradiation light from the light source array 9 is irradiated from a direction of nails of the fingers of the hand 1 of the user 1101.

<6. Example of Placement of Biometric Authentication Device and Hand at the Time of Authentication>

Figure 11:
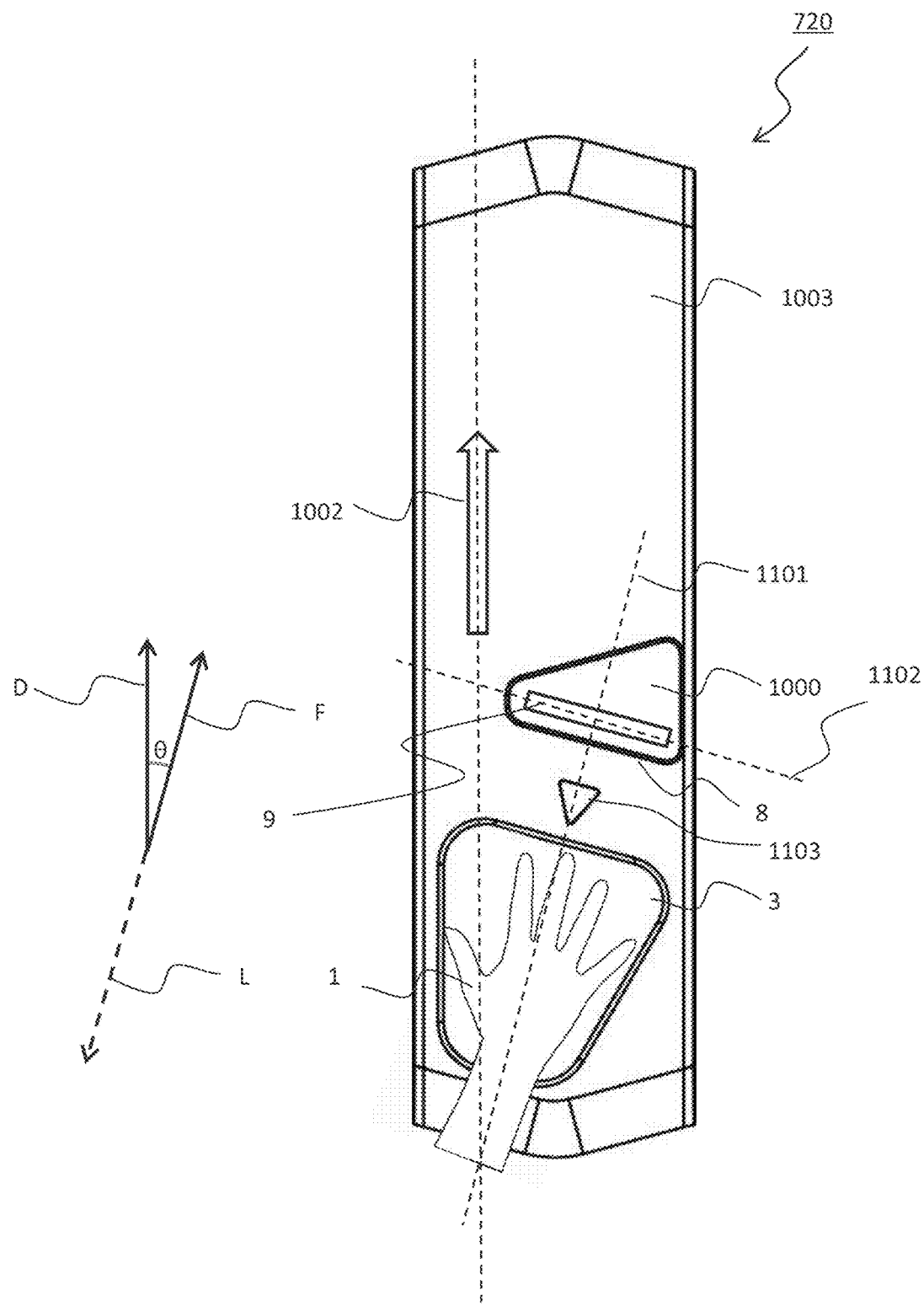
FIG. 11 is a plan view showing a situation in which the user uses the biometric authentication device according to the example of the present invention.

FIG. 11 is a plan view showing an upper surface of the housing of the biometric authentication device shown in FIG. 10 and shows a preferable placement example of the biometric authentication device 720 and the hand 1 at the time of authentication. A longitudinal direction 1101 of the fingers of the hand 1 intersects with a traveling direction 1002 of the user with an angle of less than 90 degrees. In other words, a vector D indicating the traveling direction 1002 of the user intersects with a vector F indicating the longitudinal direction of the finger heading from a root of the user's finger toward the nail with an acute angle θ. The vector L of the irradiation light irradiated from the light source array 9 is opposite to the vector F. An example of the acute angle θ can be set to, for example, 5 degrees to 20 degrees. The irradiation light may be irradiated at an angle with respect to a horizontal plane as shown in FIGS. 3 to 5 and so on. In that case, the vector L may be considered as a vector of a horizontal component (a component in a plane parallel to a floor surface).

Actually, the longitudinal direction 1101 of the fingers depends on how to place the hand of the user. Hence, in the example of FIG. 11, the biometric authentication device 720 is designed to guide the user so that the user puts the hand at a predetermined position.

For example, as shown in FIG. 11, it is conceivable that a shape of the opening 3 is configured in a trapezoidal shape that covers an expanded shape of the hand. In the example of FIG. 11, corners of the trapezoid are rounded from the viewpoint of design. The trapezoidal sides of the opening 3 are configured such that an end side (front side) of she housing 1003 is short and an opposite side (back side) is long. As shown in FIG. 11, two parallel sides of the trapezoid of the opening 3 intersect with the traveling direction 1002 of the user at the acute angle. This is because when she two parallel sides of the trapezoid intersect with the traveling direction 1002 of the user at a right angle, if the longitudinal direction of the fingers is set in parallel to the traveling direction 1002 accordingly, a burden is exerted on a wrist of the user.

In addition, in the example of FIG. 11, the placement of the light source unit 1000 is deviated from the traveling direction 1002. For example, the light source unit 1000 is placed in a direction with an acute angle θ with respect to the traveling direction 1002. With the configuration described above, when the hand 1 is placed such that the longitudinal direction of the finger is oriented in the direction of the light source unit 1000, the direction of the light source unit 1000 can be easily aligned with the longitudinal direction of the finger within a movable range of the wrist, and a burden of bending the wrist can be reduced. Further, since the light source unit 1000 is deviated from the traveling direction 1002, the hand 1 and a part of the body can be unlikely to touch the light source unit 100 when the user passes through the biometric authentication device 720.

Further, a marker (or a fingertip guide portion) 1103 indicating the longitudinal direction of the finger may be installed between the light source unit 1000 and the opening 3. When the marker 1103 is installed, the user can be guided to put the hand 1 at a predetermined position.

The traveling direction 1002 of the user also actually depends on how the user walks. How to walk and a course of the user is restricted by the placement of the biometric authentication device 703. In the example of FIG. 11, the housing 1003 of the biometric authentication device 702 restricts the traveling direction 1002 of the user and it is assumed that a long side (the longest, side) or the longitudinal direction of the housing 1003 is substantially parallel to the traveling direction 1002 of the user. If the traveling direction 1002 of the user is parallel to the longitudinal direction of the housing 1003, the traveling direction 1002 may be considered to be parallel to the side surface forming the long side of the housing 1003. In that case, the two parallel sides of the trapezoid of the opening 3 intersect with the side surfaces of the housing 1003 at an acute angle. Incidentally, although not shown in FIG. 11, the imaging unit 11 is disposed below the opening 3.

The present invention is not limited to the above configuration. In the example of FIG. 11, as an example of the configuration, when viewed from a direction perpendicular to the traveling direction 1002 of the user, the placements of the light source unit 1000 and the opening 3 do not overlap with each other. The opening 3 is disposed on a front side of the user in the traveling direction, and the light source unit 1000 is disposed on a far side of the user in the traveling direction.

As for the vector L of the irradiation light, as shown lei FIG. 8, when there are the multiple point light sources 10 in the light source array 9, the irradiation light of all the point light sources may be aligned with the vector L, or only the irradiation light may be aligned with the vector L. However, in order to capture an excellent image, it is desirable to align the irradiation light (or the projection onto the floor surface) of a majority of the point light sources with the vector L.

When the point light sources 10 are formed of LEDs or the like, it is easy to arrange the LEDs so that the light from the LEDs is emitted perpendicularly to a substrate on which the LEDs are mounted. Therefore, when the irradiation light of the majority point light sources is aligned with the vector L, it is desirable that an orientation 1102 of a plane formed by the light source array 9 is substantially perpendicular to the longitudinal direction 1101 of the fingers. The substrate on which the LEDs are mounted is usually parallel to the plane formed by the light source array 9 including the point light sources 10.

Although not intended to be limited, in the present example, since the plane formed by the light source array 9 is parallel to the plane of the opening 8, the direction of projection of a vector perpendicular to the plane of the opening 8 onto the floor surface may be considered as the longitudinal direction 1101 of the fingers. In the present example, since the two parallel sides of the trapezoid of the opening 3 are parallel to the surface of the opening 8 (or the projection onto the floor surface), the direction perpendicular to the two parallel sides of the trapezoid of the opening 3 may be considered as the longitudinal direction 1101 of the fingers.

Figure 12:
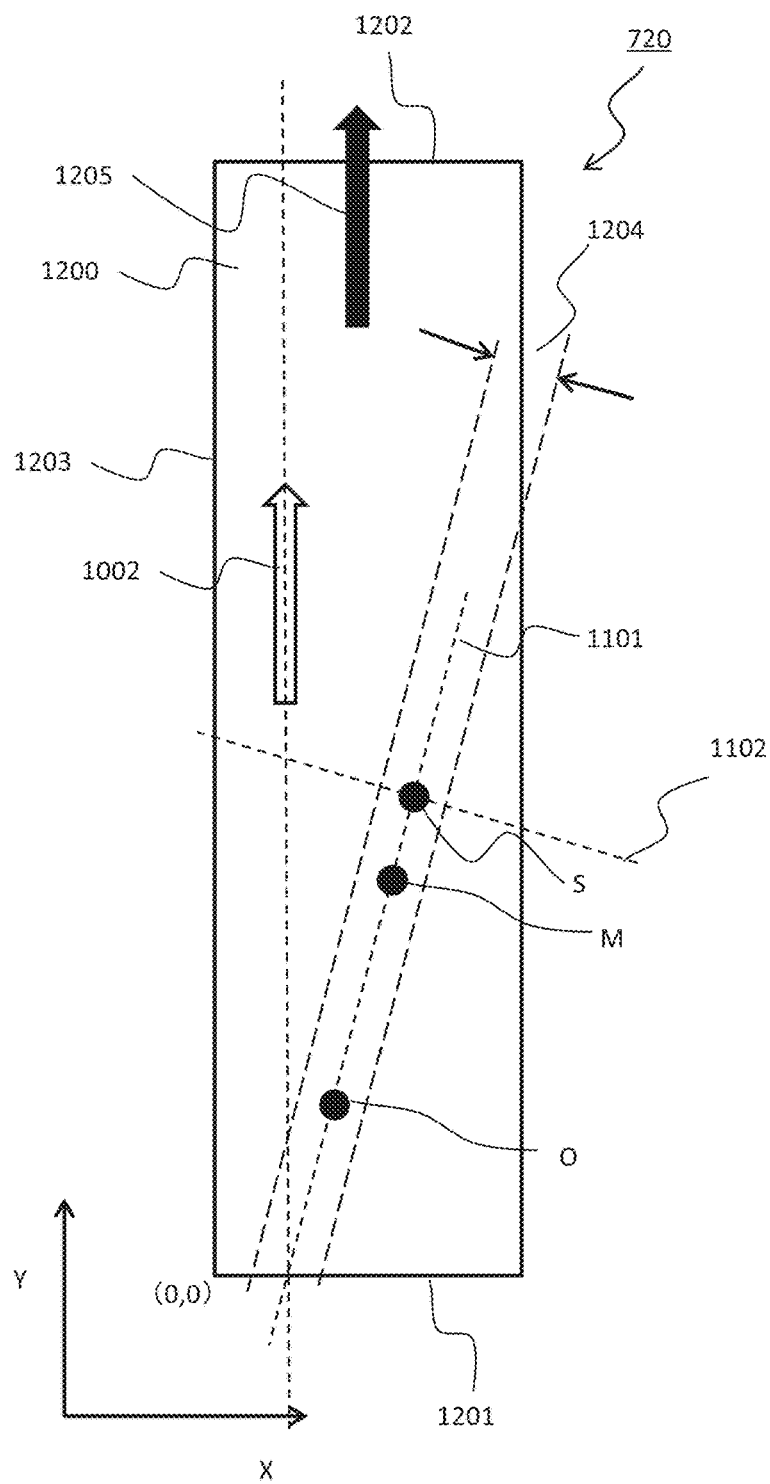
FIG. 12 is a plan view showing a placement example of a configuration of the biometric authentication device according to the example of the present invention.

FIG. 12 shows an example of a design rule of a geometric placement of the respective elements of the biometric authentication device 720 in consideration of the above configuration. The housing 1003 of the biometric authentication device 720 can be designed such that the corners are rounded and side surfaces and a top surface are configured by multiple planes or curved surfaces as actually shown in FIG. 10 and FIG. 11. However, if the multiple surfaces or curved surfaces are approximated to a plane by a known technique, the biometric authentication device 720 is basically of a rectangular parallelepiped shape.

FIG. 12 shows a projection 1200 of the housing 1003 onto a floor surface when the casing 1003 of the biometric authentication device 720 is approximated to a rectangular parallelepiped. In this case, it is assumed that the floor surface is a virtual surface on which the housing 1003 is installed. The floor surface is usually a surface perpendicular to the direction of gravity. An upper surface of the housing is a surface parallel to the floor surface on a side opposite to the floor surface. In this case, among four side surfaces of the housing 1003, a side surface on the front side of the user in the traveling direction 1002 is defined as a front side surface, an opposite side of the front side surface is defined as a rear side surface, and a right or left as viewed from the front side surface side is defined as a passage side surface facing a user's passage. A front side plane projection 1201, a rear side plane projection 1202, and a passage side plane projection 1203 (in this example, the left side is the passage side surface) are shown in FIG. 12. The passage side surface is usually a side surface configuring a long side of the housing (the longest side in the projection of the housing on the floor surface).

In this case, coordinates are set with an axis parallel to the front, side plane projection 1201 as an X axis and an axis parallel to the passage side plane projection 1203 as a Y axis, and an intersection of the front side plane projection 1201 and the passage side plane projection 1203 is set as an origin (0, 0). A projection of the geometric center of gravity of the opening 3 of the biometric authentication device 720 onto the floor surface is defined as O and coordinates of the projection S are defined as (XO, YO). Moreover a projection of the geometric center of gravity of the light source onto the floor surface is defined as S, and coordinates of the projection S are defined as (XS, YS). In that case, XS>XO>0 and YS>YO>0 are satisfied in the present design rule.

The opening 3 may be a plane or a curved surface, and if the opening 3 is the curved surface, the curved surface may be approximated to a plane by a known technique to obtain the geometric center of gravity. In addition, in the case where the light source is a light source array in which the point light sources 10 are two-dimensionally arrayed as shown in FIG. 8, the geometric center of gravity of the light source may be the geometric center of gravity of the surface formed by the light source array. The point light sources 10 of the light source array 9 may be disposed in a plane or may be disposed in a curved shape. When the point light sources 10 are disposed in the curved shape, the curved shape may be approximated to the plane by the known technique to obtain the geometric center of gravity. In addition, for example, in the example of FIGS. 10 and 11, the light sources of the light source array 9 may be placed in a plane perpendicular to the floor surface. Alternatively, the light sources may be placed in a plane or a curved surface inclined at an acute angle to the floor surface.

Moreover, when the marker 1103 is installed, a projection of the geometric center of gravity of the marker 1103 onto the floor surface is defined as M, and coordinates of the marker 1103 are defined as (XM, YM). In that case, although not limited, as an example of the design rule, XS>XM>XO>0 and YS>YM>YO>0 can be satisfied.

When there are the projection O of the geometric center of gravity of the opening 3, the projection S of the geometric center of gravity of the light sources of the light source array 9, and the marker, it is desirable that the projection M of the geometric center of gravity of the marker 1103 is aligned with the projection O and the projection S. However, there is no need to strictly place those projections on a straight line. For example, those projections can be placed in a straight belt-shaped area of about 3 cm in width.

In the present design rule, the traveling direction 1002 of the user may be regarded as equivalent to the longitudinal direction 1205 of the housing 1003 in relation to the housing 1003 of the biometric authentication device 720. Also, when the housing 1003 is approximated to a rectangular parallelepiped, the longitudinal direction 1205 of the housing 1003 can be regarded as the direction of the passage side plane projection 1203.

FIGS. 11 and 12 show an example in which the user passes through the left side of the biometric authentication device 720 in the drawing. Alternatively, the biometric authentication device 720 may be configured so that the user passes through the right side of the biometric authentication device 720. In that case, it is needless to say that the biometric authentication device 720 may be configured such that the right and left of the biometric authentication device 720 are reversed.

<7. Application Example of Biometric Authentication Device to Gate Device>

Figure 13:
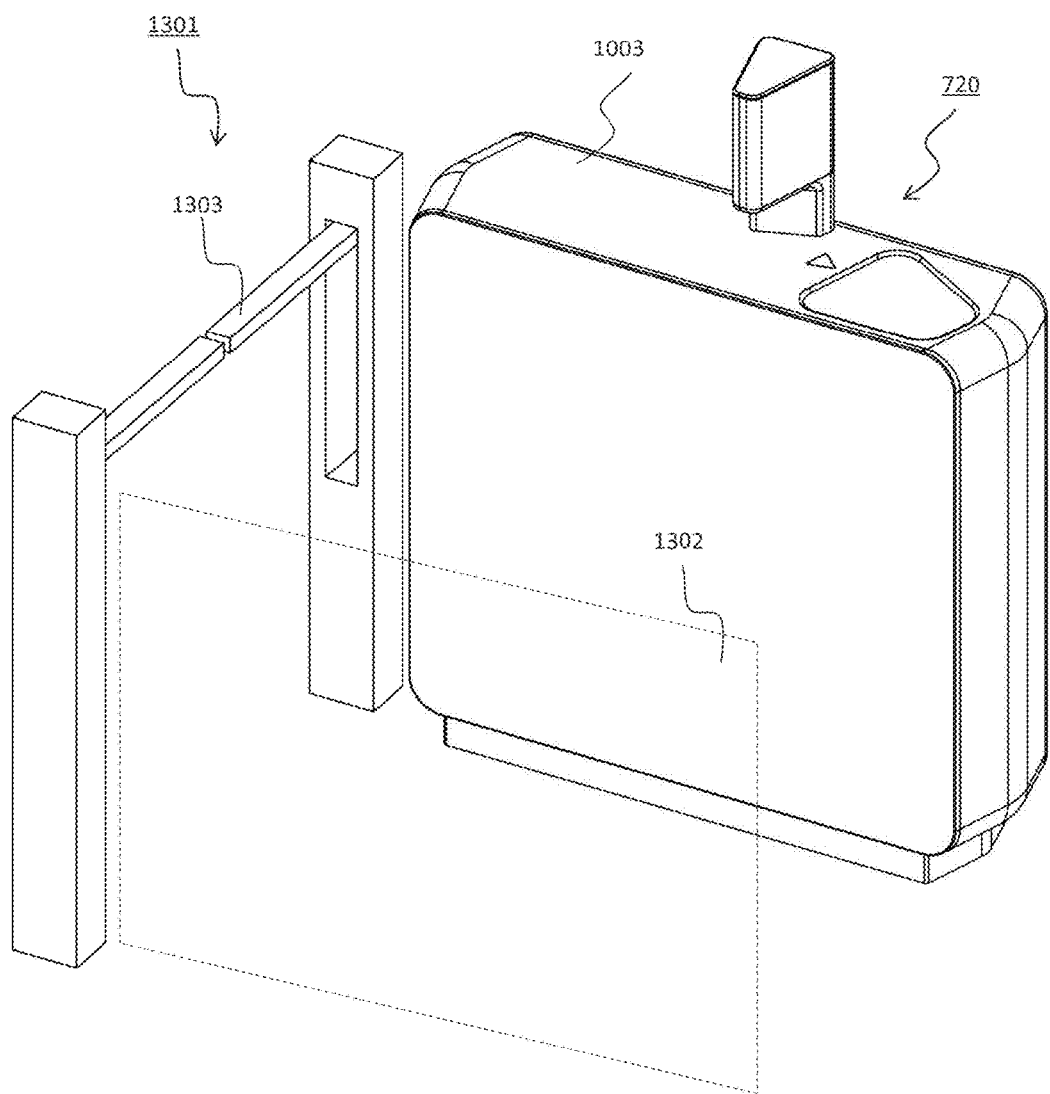
FIG. 13 is a perspective view of the biometric authentication device provided with a gate according to the example of the present invention (when closed).

FIG. 13 shows an example in which a gate device 1301 for physically permitting or rejecting entry of the user is provided in the biometric authentication device 720 in FIG. 10. The user is led to a space (passage) sandwiched between the housing 1003 of the biometric authentication device 720 and a wall surface 1302, and performs authentication by the biometric authentication device 720. If the authentication is successful, a bar 1303 of the gate device 1301 is released and the user can pass through the gate. FIG. 13 shows a state in which the gate is closed by the bar 1303. Meanwhile, the multiple biometric authentication devices 720 can be arranged in parallel. In that case, the wall surface 1302 can be configured by a side surface of a housing of another adjacent biometric authentication device.

Figure 14:
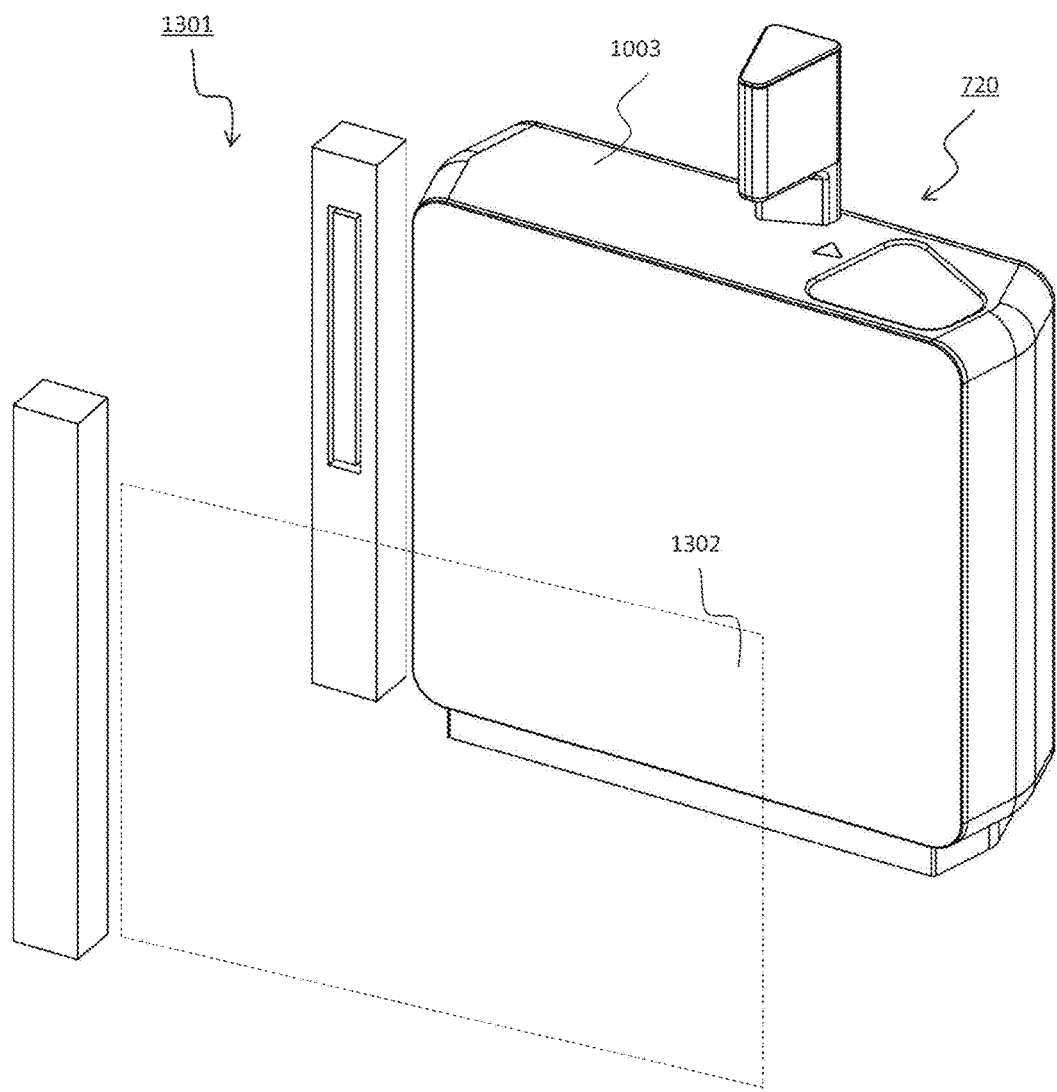
FIG. 14 is a perspective view of the biometric authentication device provided with a gate according to the example of the present invention (when opened).

FIG. 14 shows a state in which the authentication is successful in the device of FIG. 13 and the bar of the gate device 1301 is opened. In that state, the user can enter inside of the gate. In the gate device 1301, instead of providing the bar 1303, a device for generating an alarm by sound or light at the time of authentication failure or a device for capturing an image may be provided. In addition, the bar 1303 may be of a different configuration such as a door type, for example, an automatic door.

<8. Configuration Example of Opening of Biometric Authentication Device>

Figure 15:
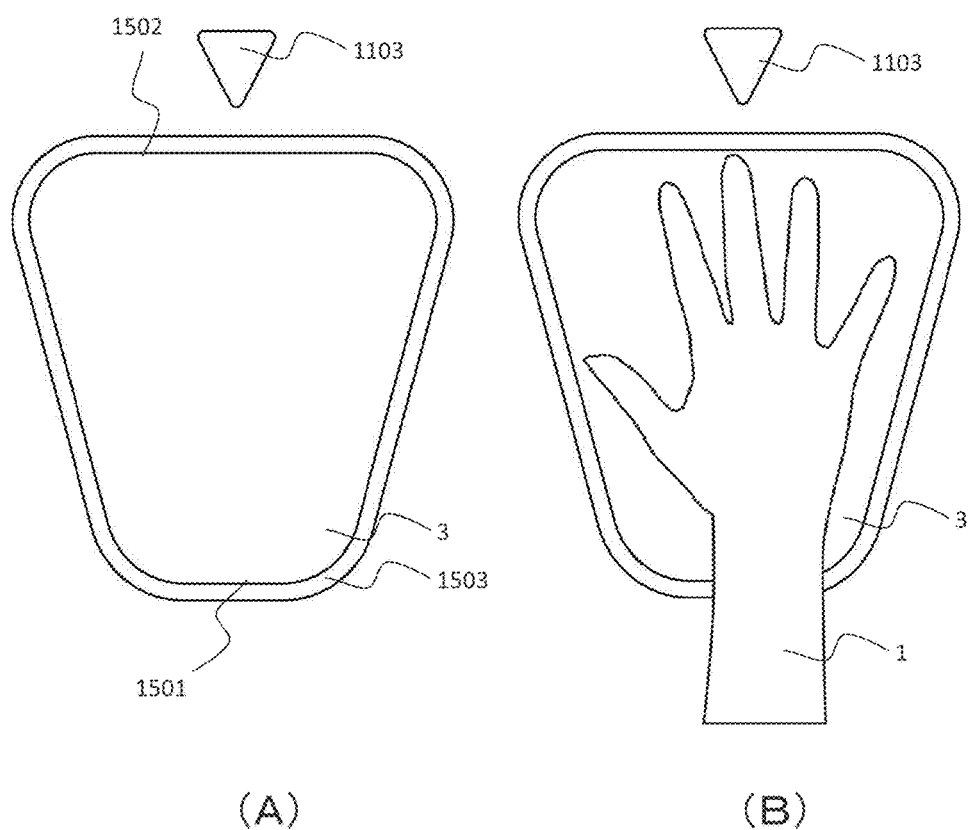
FIGS. 15A and 15B are plan views showing one example of an opening of the biometric authentication device according to the example of the present invention.

FIGS. 15A and 15B are plan views showing details of the opening 3 of the biometric authentication device 720 in FIG. 10. FIG. 15A shows the details of the opening 3 and FIG. 15B shows a state in which the hand 1 is placed on the opening 3. In the example of FIGS. 15A and 15B, the opening 3 is formed in a trapezoidal shape whose corners are curved so as to cover the overall hand 1, and configured such that a short side 1501 of two parallel sides is located at a front and a long side 1502 is located at a back side of the opening 3. The marker 1103 may be disposed at the back side of the opening 3 so as to indicate the longitudinal direction of the fingers of the hand 1. An LED or the like can be disposed on the marker 1103 or an edge (or a hand posture and position guide portion) 1503 of the opening 3, so as emit light with a color or a pattern according to a processing situation. For example, the LED blinks with blue for waiting, green for authentication success, and red for authentication rejection and error.

The surface of the opening 3 may be located slightly below an edge 1503. The edge 1503 may be formed convexly from an upper surface of the opening 3 or the housing 1003. If a height difference is present between the opening 3 and the edge 1503, a light emission state of the LED or the like is visible from a resultant stepped surface, and the visibility is improved.

Figure 16:
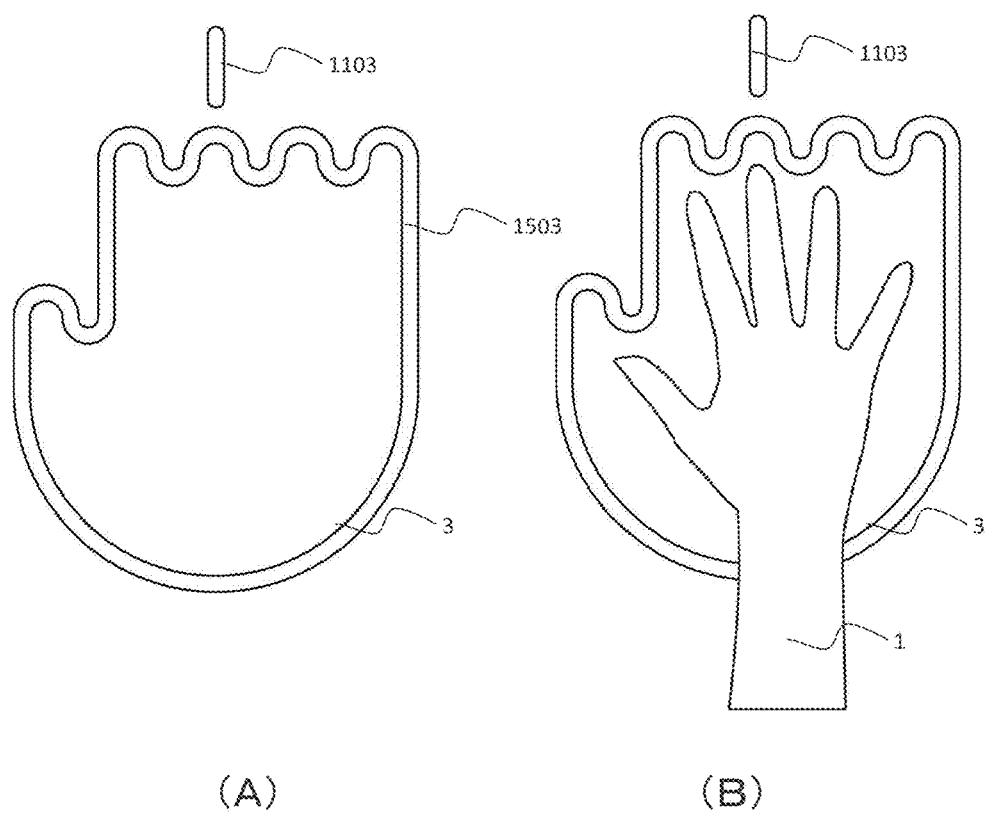
FIGS. 16A and 16B are plan views showing another example of the opening of the biometric authentication device according to the example of the present invention.

FIGS. 16A and 16B are plan views showing another example of the opening 3 of the biometric authentication device 720. FIG. 16A shows details of the opening 3 and FIG. 16B shows a state in which the hand 1 is placed on the opening 3. In the example of FIGS. 16A and 16B, the opening 3 has a shape similar to the shape of the hand 1, and the back side of the opening 3 has a shape imitating the fingers of the hand. The marker 1103 may be provided on the far side of the opening 3 so as to indicate a position where the hand 1 is placed. The other configurations are the same as those in the example of FIGS. 15A and 15B.

Figure 17:
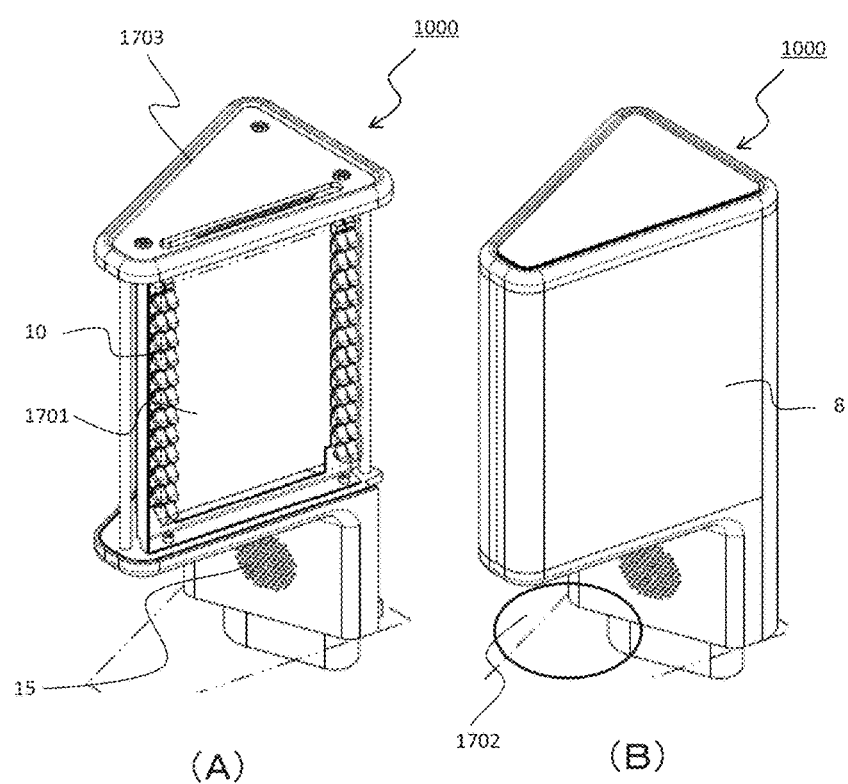
FIGS. 17A and 17B are perspective views showing an example of a light source unit of the biometric authentication device according to the example of the present invention.

FIGS. 17A and 17B are perspective views showing details of the vicinity of the opening 8 of the light source unit 1000 in the biometric authentication device 720 of FIG. 10. As described in FIGS. 1 and 2, a cover made of acrylic, glass, or the like is used for the opening 8, and the cover can cut a visible light so that the inside of the device cannot be seen from the user. FIG. 17A shows a state in which the cover of the opening 8 of the light source unit 1000 is removed, and FIG. 17B shows a state in which the cover of the opening 8 is attached.

As shown in FIG. 17A, the point light sources 10 are two-dimensionally arrayed inside the device. In FIG. 17A, a part of the point light sources 10 is omitted so that an LED substrate 1701 behind the point light sources 10 is visible.

A notch is provided in a portion (base) where the light source unit 1000 rises from an upper surface of the biometric authentication device 702 to form a space 1702. With the provision of the space 1702, after the authentication, the user can move across the space 1702 while holding the hand 1 over the opening. In addition, the speaker 15 can be installed in the notch of the light source unit 1000 and the speaker 15 can be disposed in an inconspicuous position.

A heat radiation hole 1703 can be provided in a top portion of the light source unit 1000. The heat radiation hole 1703 in the top portion of the light source unit 1000 enables exhaust heat from a position where a hot air is not applied to the user.

Figure 18:
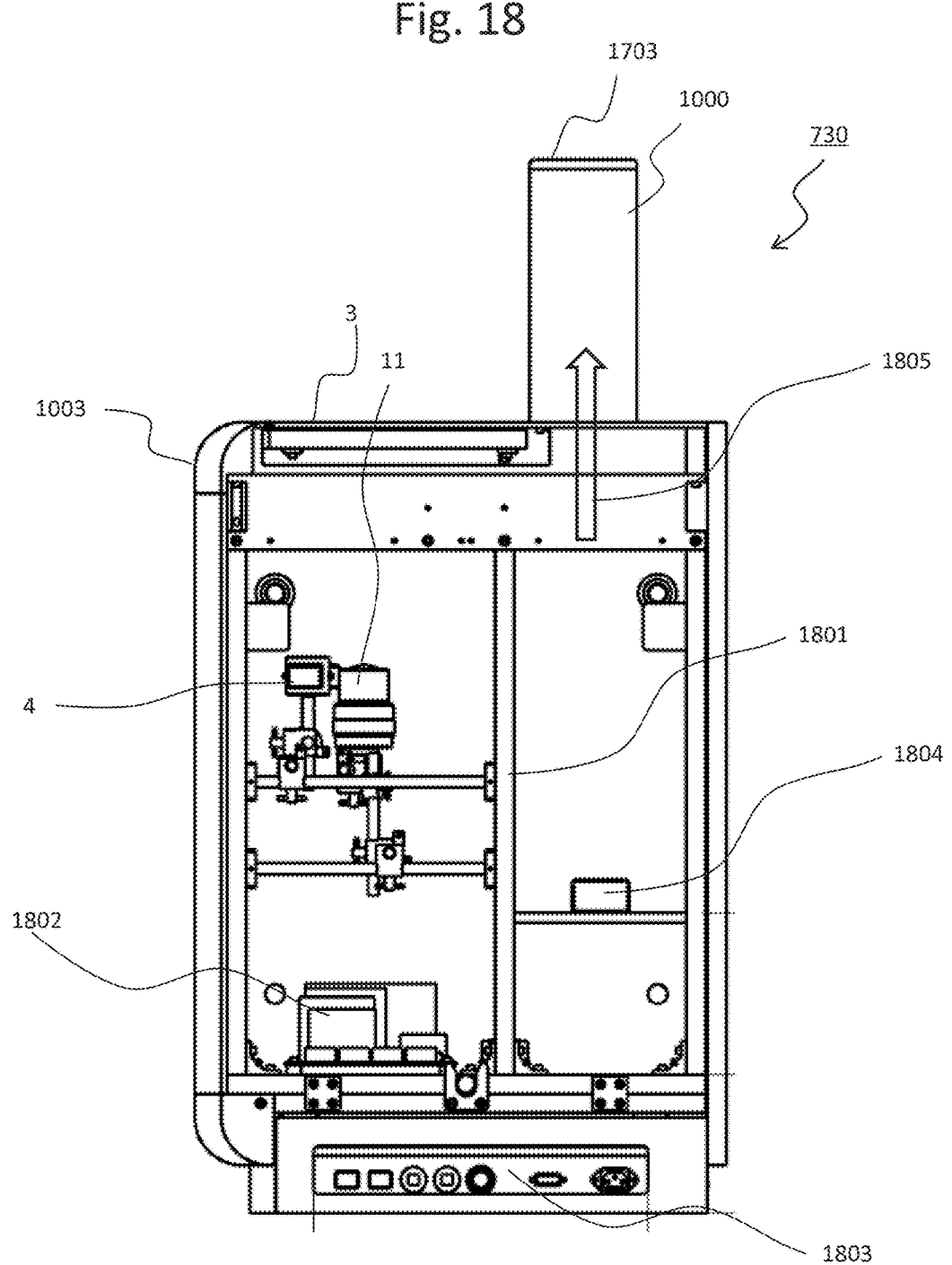
FIG. 18 is a side view showing an internal configuration example of a registration device according to the example of the present invention.

FIG. 18 is an internal transparent side view showing an internal configuration of the registration device 730 as viewed from the passage side. As described above, since the biometric authentication device 720 and the registration device 730 can have a common configuration except for the presence or absence of the authentication function, the configuration of FIG. 18 can be similarly applied to the biometric authentication device 720.

The light source unit 1000 is installed on an upper surface of the registration device 730 so that light can be irradiated to the hand placed on the opening 3. The light that has transmitted through the hand is imaged by the imaging unit 11 to acquire a pattern of the finger vein. The distance sensor 4 is used for optically detecting the position of the hand. The interior of the housing 1003 is reinforced with a frame 1801 as necessary, and includes a power supply 1802 and an I/O terminal 1803. The interior of the housing 1003 includes a circuit unit 1804 with the computer 5, the memory 6, the CPU 7, and the like.

Air can be moved inside the housing 1003 and the Might source unit 1000, and an exhaust heat 1805 inside the housing 1003 is discharged from an exhaust hole 1703 through the light source unit 1000.

Figure 19:
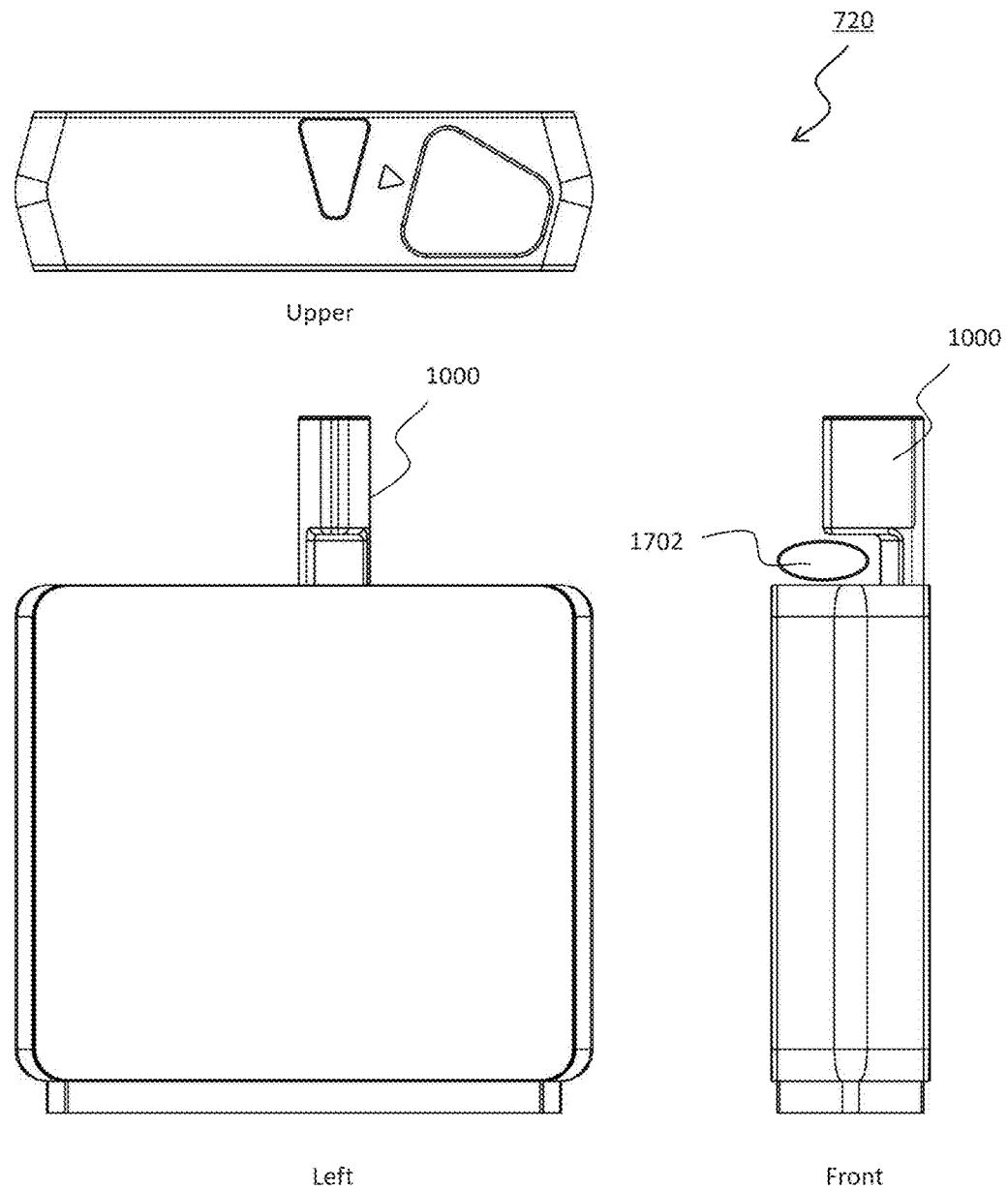
FIG. 19 is a three-view diagram showing an example of the biometric authentication device according to the example of the present invention.

FIG. 19 is a three-view diagram of the biometric authentication device 720 in FIG. 10. As described with reference to FIG. 12, from a point of view of the user to be authenticated, the biometric authentication device 720 includes a front side surface (Front), a left side surface (Left) that is a passage side surface forming the left side surface of the front side face, and an upper surface (Upper) that is an upper side portion of the housing 1003. As described with reference to FIGS. 17A and 17B, the space 1702 is provided on the side of the passage side surface of the light source unit 1000.

Figure 20:
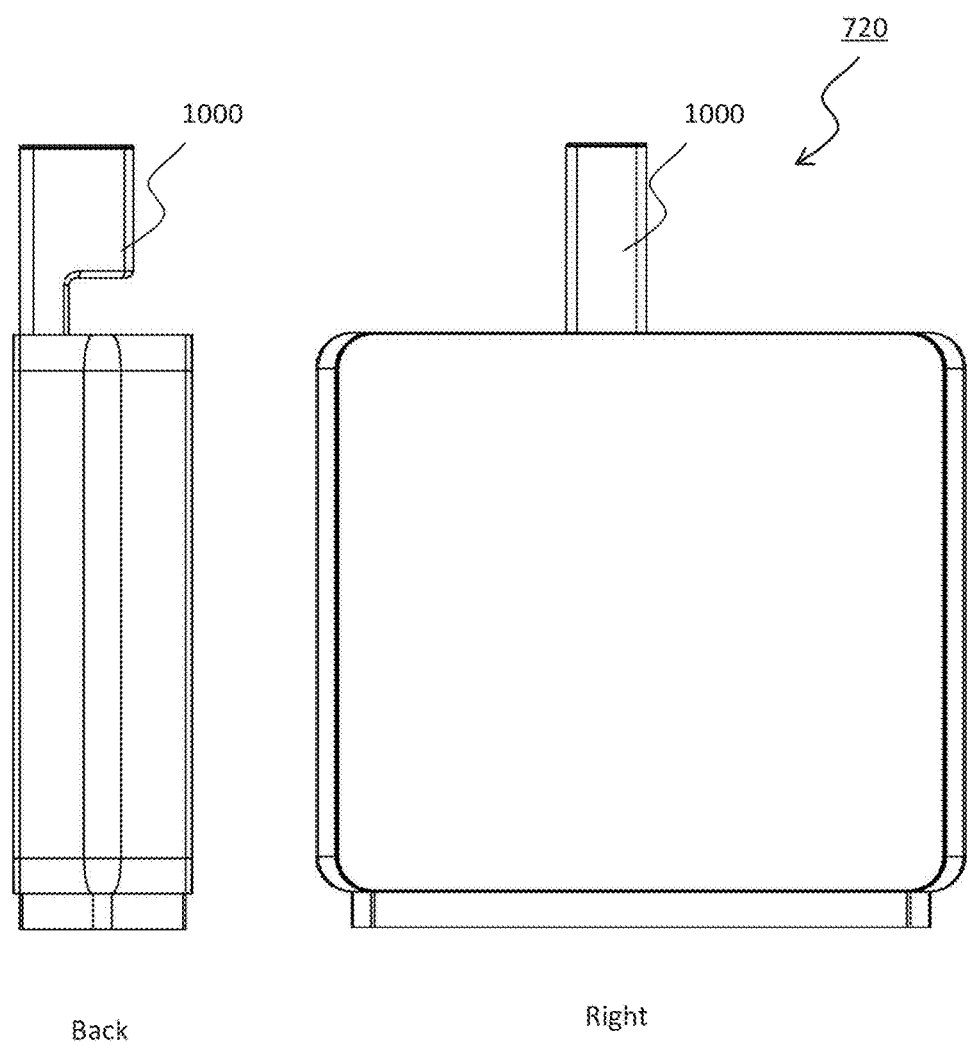
FIG. 20 is a two-view diagram showing an example of the biometric authentication device according to the example of the present invention.

FIG. 20 is a two-view diagram of the biometric authentication device 720 in FIG. 10. A facing surface of the passage side surface (Left) is a right side surface (Right), and a facing surface of the front side surface (Front) is a back side surface (Back).

Figure 21:
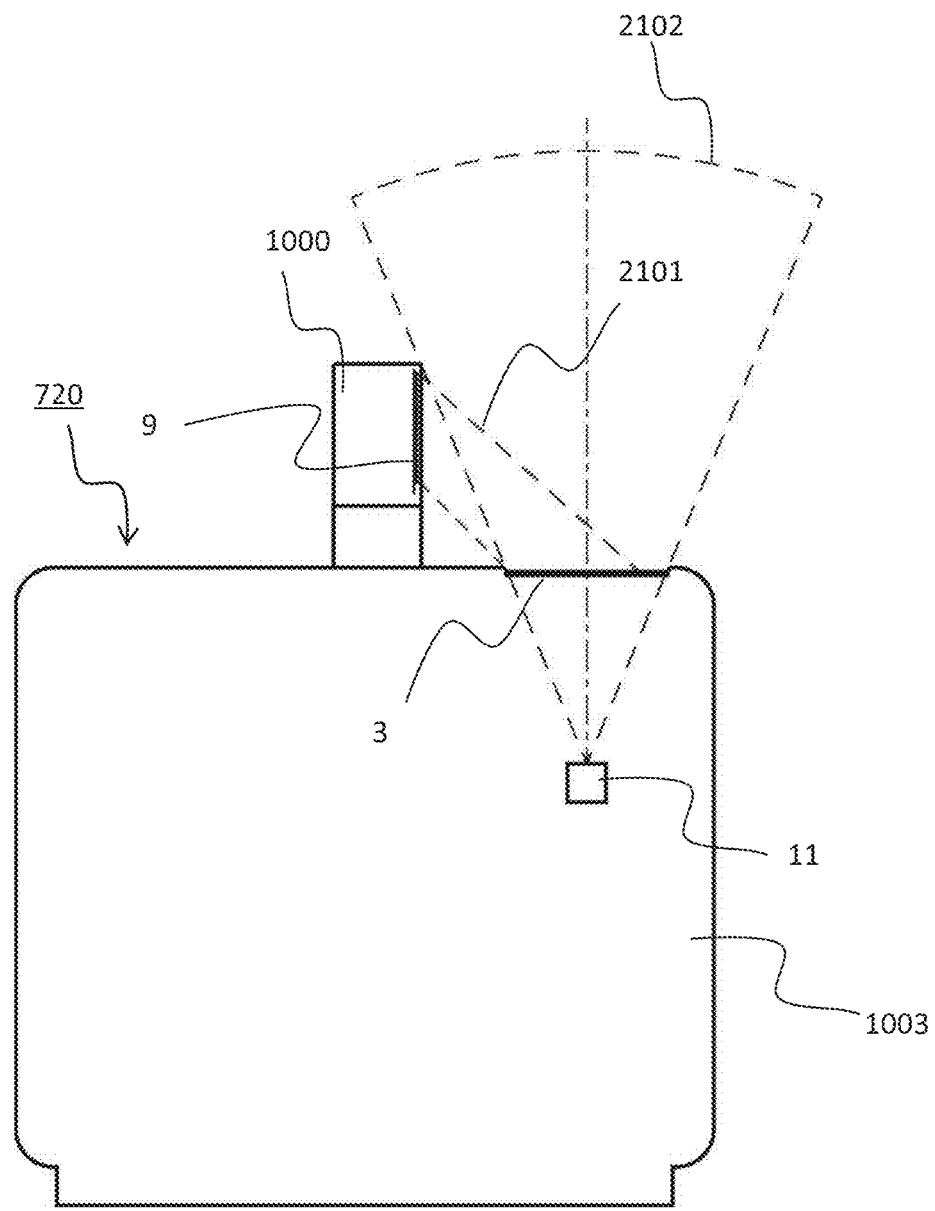
FIG. 21 is a side view showing an example of a case in which a light source array is placed outside an angle of view of an imaging unit.

FIG. 21 is a side view showing a positional relationship between the light source array 9 and the imaging unit 11 of the biometrics authentication device 720 in FIG. 10. The placement positions of the respective point light sources 10 configuring the light source array 9 are not in a direction substantially perpendicular to the face of the opening 3 as shown in FIG. 2, but may be tilted. However, in any case, it is desirable that the point light sources 10 are not reflected within an angle of view 2102 of the imaging unit 11 (in other words, an imaging area of the imaging unit 11) and within an angle of view of the distance sensor 4 (not shown in FIG. 21) (in other words, a detection area of the distance sensor 4).

In other words, as shown in FIG. 21, it is desirable that the light source array 9 is disposed outside the angle of view of a camera or the like configuring the imaging unit 11. When the light source array 9 is reflected within the angle of view 2102 of the imaging unit 11, the tight source portion becomes brighter when the light source array 9 is turned on, and a luminance saturation occurs, which may deteriorate the clarity of the whole blood vessel image. This is a phenomenon peculiar to the light sources of the image acquisition device 2 that the multiple light sources are arrayed in a lattice pattern in a direction perpendicular to the installation surface of the housing 1003 so that the light sources are likely to be reflected within the angles of view of the imaging unit 11 and the distance sensor 4. With the prevention of the reflection of the light source array 9, a clear blood vessel image can be captured. Likewise, when the light source array 9 is reflected within the angle of view of the distance sensor 4, the accuracy of the position detection and the posture detection of the hand and the fingers may be deteriorated with the inclusion of more nose. Therefore, it is desirable to prevent the reflection of the point light sources 10 and prevent the accuracy deterioration of the position detection and the posture detection of the hand and the fingers.

Figure 22:
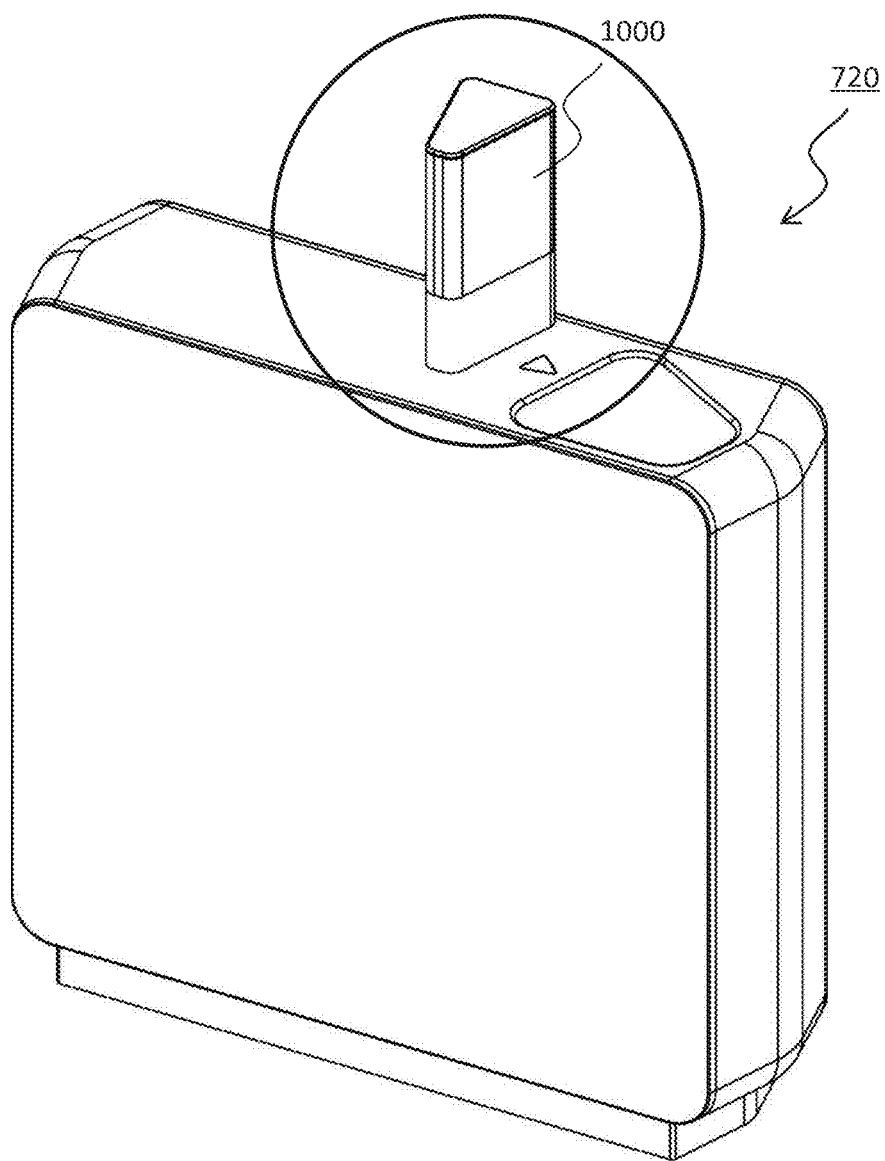
FIG. 22 is a perspective view showing another example of the biometric authentication device according to the example of the present invention.

FIG. 22 shows another configuration example of the light source unit 1000. Unlike the examples shown in S. 17 and 19, no space 1702 is provided on the side of the passage side surface of the light source unit 1000. Even in such a configuration, the position of the light source unit 1000 is adjusted, to thereby enable the authentication operation without any problems.

The present invention is not limited to the respective embodiments described above, but includes various modifications. For example, a part of one configuration example can be replaced with another configuration example, and the configuration of one example can be added with the configuration of another example. Moreover, in a part of the respective configuration examples, another configuration can be added, deleted, or replaced.

INDUSTRIAL APPLICABILITY

In particular, the present invention can be used for devices using biometric authentication of a hand, a finger, or the like.

REFERENCE SIGNS LIST

1: hand,
2: Image acquisition device,
3: opening,
4: distance sensor,
5: computer,
6: memory,
7: CPU,
8: opening,
9: light source array,
10: point light source,
11: imaging unit,
12: optical filter,
13: interface,
14: storage device,
15: speaker,
16: display,
17: visible light source,
18: keyboard,
19: blood vessel image,
20: vessel,
21: luminance saturation region,
50: data input unit,
51: light source control unit,
52: image input unit.

The invention claimed is:

1. A biometric authentication device comprising:
a housing having a front side surface, a rear side surface, a passage side surface and an upper surface;
a light source array that is installed on the upper surface of the housing and includes a plurality of light sources;
an opening that is provided in the upper surface of the housing and located between the light source array and an intersection of the front side surface and the upper surface;
an infrared camera that is disposed inside the housing below the opening in the upper surface; and
a processor, wherein
an optical axis of a majority of the light sources intersects with the upper surface of the housing at an angle less than 90 degrees,
a plane formed by the light source array intersects with the passage side surface of the housing at an angle of less than 90 degrees, and
the processor is programmed to perform authentication of a biometric feature of a user irradiated with an irradiation light from the light sources and imaged by the infrared camera through the opening.

2. The biometric authentication device according to claim 1, wherein
the light sources are a plurality of point light sources which are two-dimensionally arranged.

3. The biometric authentication device according to claim 1, wherein
the light source array is installed on the upper surface of the housing and does not overlap with the opening in the upper surface of the housing, and
a geometric center of the opening and a geometric center of the light source array define a line which is substantially perpendicular to the plane formed by the light source array.

4. The biometric authentication device according to claim 1, wherein
a marker is placed on the upper surface of the housing between the opening and the light source array.

5. The biometric authentication device according to claim 1, wherein
a shape of the opening is substantially trapezoidal and is configured to be larger than a hand of the user, and
the processor is programmed to perform authentication of a biometric feature of the hand of the user irradiated with the irradiation light from the light sources and imaged by the infrared camera through the opening.

6. The biometric authentication device according to claim 1, wherein
a shape of the opening imitates a shape of a human hand and is configured to be larger than the human hand, and
the processor is programmed to perform authentication of a biometric feature of the human hand irradiated with the irradiation light from the light sources and imaged by the infrared camera through the opening.

7. The biometric authentication device according to claim 1, wherein
the light sources of the light source array are not included in an imaging area of the infrared camera.

8. The biometric authentication device according to claim 1, wherein
the light source array has a base which includes a notch between the light sources and the upper surface of the housing, and the notch faces the passage side surface of the housing.

* * * * *